United States Patent
Turnlund et al.

(10) Patent No.: US 6,296,603 B1
(45) Date of Patent: Oct. 2, 2001

(54) RADIOACTIVE INTRALUMINAL ENDOVASCULAR PROSTHESIS AND METHOD FOR THE TREATMENT OF ANEURYSMS

(75) Inventors: Todd H. Turnlund, Sunnyvale; William L. Sweet, Mountain View, both of CA (US)

(73) Assignee: IsoStent, Inc., Belmont, CA (US)

( * ) Notice: Subject to any disclaimer, the term of this patent is extended or adjusted under 35 U.S.C. 154(b) by 0 days.

(21) Appl. No.: 09/084,675

(22) Filed: May 26, 1998

(51) Int. Cl.$^7$ .................................................. A61N 5/00
(52) U.S. Cl. ......................................................... 600/3
(58) Field of Search ............................. 600/1–8; 606/78, 606/108, 191–198

(56) References Cited

U.S. PATENT DOCUMENTS

| | | |
|---|---|---|
| 4,733,665 | 3/1988 | Palmaz . |
| 5,059,166 | 10/1991 | Fischell et al. . |
| 5,102,417 | 4/1992 | Palmaz . |
| 5,176,617 | 1/1993 | Fischell et al. . |
| 5,195,984 | 3/1993 | Schatz . |
| 5,653,736 | 8/1997 | Glastra . |
| 5,697,971 | 12/1997 | Fischell et al. . |
| 5,709,644 * | 1/1998 | Bush .......................................... 600/3 |
| 5,840,009 * | 11/1998 | Fischell et al. ............................ 600/3 |
| 5,871,437 * | 2/1999 | Alt ............................................. 600/3 |
| 5,901,102 * | 6/1999 | Hastings .................................... 600/3 |

OTHER PUBLICATIONS

Wiedermann et al., "Intracoronary Irradiation Markedly Reduces Neointimal Proliferation After Balloon Angioplasty in Swine: Persistent Benefit at 6–month Follow–Up", JACC, vol. 25, No. 6, May 1995, pp. 1451–1456.

Kovalic, et al., "Radiation Therapy Following Keloidectomy: A 20–Year Experience", Int. J. Radiation Oncology, Biol. Phys., vol. 17, pp. 77–80, Jan. 1989.

Ayers et al., "The Prevention of Heterotopic Ossification in High–Risk Patients by Low–Dose Radiation Therapy After Total Hip Arthroplasty", The Journal of Bone and Joint Surgery, Incorporated, vol. 68–A, No. 9, Dec. 1986.

Berson et al., "Radiotherapy for Age–Related Macular Degeneration: Preliminary Results of a Potentially New Treatment", Int. J. Radiation Oncology Biol. Phys., vol. 36, No. 4, pp. 861–865, 1996.

Weinberger et al., "Intracoronary Irradiation: Dose Response for the Prevention of Restenosis in Swine", Int. J. Radiation Oncology Biol. Phys., vol. 36, No. 4, pp. 767–775, 1996.

(List continued on next page.)

Primary Examiner—John P. Lacyk
(74) Attorney, Agent, or Firm—Beyer Weaver Thomas & Nguyen, LLP

(57) ABSTRACT

A method for increasing the rate of thrombus formation and/or proliferative cell growth of a selected region (21) of cellular tissue (22) including the step of endovascularly irradiating the selected region (21) with radiation, having a dose range of endovascular radiation of about 1 Gy to about 600 Gy at a low dose rate of about 1 cGy/hr to about 320 cGy/hr, to increase thrombus formation and/or cell proliferation of the affected selected region (21). Preferably, the delivery means includes a deformable endovascular prosthesis (25) adapted for secured positioning adjacent to the selected region (21) of cellular tissue (22), and a radioactive source. This source cooperates with the deformable endovascular device (25) in a manner endovascularly irradiating the selected region with radiation, having the above-indicated dose range and low dose rate of endovascular radiation to increase thrombus formation and/or cell proliferation of the affected selected region (21).

58 Claims, 8 Drawing Sheets

OTHER PUBLICATIONS

Virmani, "Effects of High, Intermediate, and Low Dose Radiation on Pig Coronary Arteries", Mar., 1998, Syllabus for Advances in Cardiovascular, Radiation Therapy II Convention.

"High Activity 32P Stents Promote the Development of Atherosclerosis at Six Months in a Porcine Coronary Model", Sep. 28, 1997, Syllabus for Transcatheter Cardiovascular Therapeutics Symposium.

Carter, "Animal Studies with Beta Emitting Stents: Long Term and P–32 versus 90–Y". Mar., 1998, Syllabus for Advance in Cardiovascular Radiation Therapy II Convention.

Bedich, "Embolization of Intracranial Aneurysms with the use of Guglielmi Detachable Coils", Summer 1996, *AVIR Interventional Informer*, pp. 14, 15, 17.

B.T. Katzen, "Current status of endovascular stent grafts: an overview of applications and devices", 1997, *Textbook of Metallic Stents*, pp. 73–89, Isis Medical Media, Oxford.

Fischell, et al., "Low–Dose, B–Particle Emission from 'Stent' Wire Results in Complete, Localized Inhibition of Smooth Muscle Cell Proliferation", Dec., 1994, *Circulation*, vol. 90, No.6.

A. J. Carter, D.O. and J. R. Laird, M.D., "Experimental Results with Endovascular Irradiation via a Radioactive Stent", 1996, *Int. J. Radiation Oncology Biol. Phys.*, vol. 36, No. 4, pp. 797–803.

Laird, et al., "Inhibition of Neointimal Proliferation with Low–Dose Irradation From a B–Particle–Emitting Stent", Feb. 1, 1996, *Circulation*, vol. 93, No. 3.

Hoopes, et al., "Intraoperative Irradiation of the Canine Abdominal Aorta and Vena Cava", May, 1987, *Int.J.Radiation Oncology Biol. Phys.*, vol. 13, No. 5, pp. 715–722.

M.B. Kahaleh, "The role of vascular endothelium in fibroblast activation and tissue fibrosis, particularly in scleroderma (systemic sclerosis) and pachydermoperiostosis (primary hypertrophic osteoarthropathy)" 1992, *Clinical and Experimental Rheumatology*, 10 (Suppl. 7) pp. 51–56.

Lindsay, et al., "Aortic Arteriosclerosis in the Dog After Localized Aortic Irradiation with Electrons", Jan. 1962, *Circulation Research*, vol. X, pp. 61–67.

Lindsay, et al., "Aortic Arteriosclerosis in the Dog After Localized Aortic X–Irradiation", Jan. 1962, *Circulation Research*, vol. X, pp. 51–60.

Murayama, et al., "Ion Implementation and Protein Coating of Detachable Coils for Endovascular Treatment of Cerebral Aneurysms: Concepts and Preliminary Results in Swine Models", Jun. 1997, *Neurosurgery*, vol. 40, No. 6, pp. 1233–1244.

Langberg, et al., "Expression of fibrogenic cytokines in rat small intestine after fractionated irradiation", 1994, *Radiotherapy & Oncology* 32, pp. 29–.36.

Duckwiler, et al., "Catheters, embolic agents spark neurointervention", May 1994, *Diagnostic Imaging*, pp. 66–72, 102.

* cited by examiner

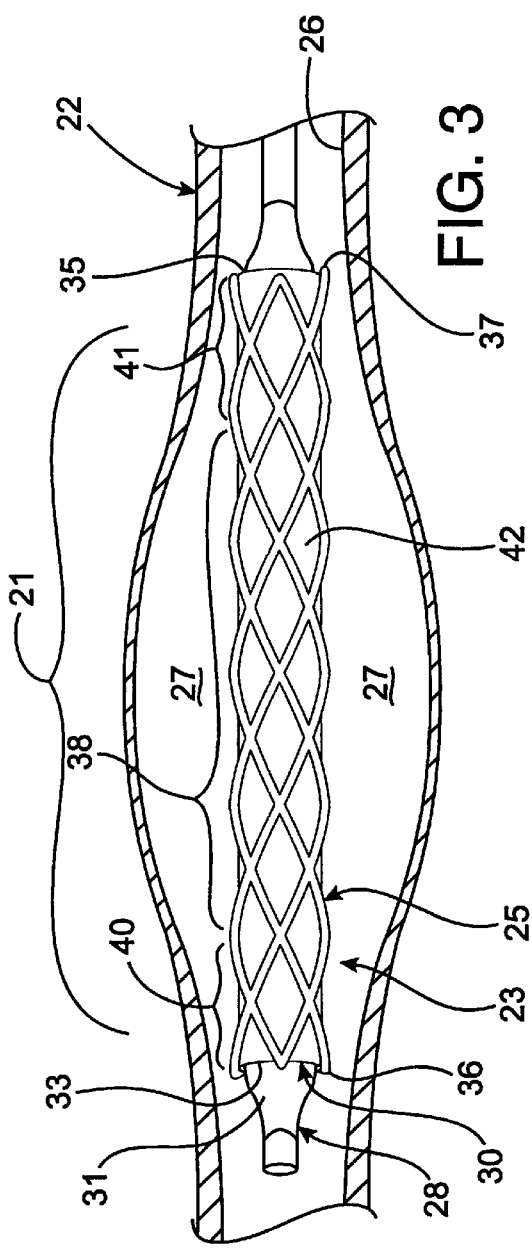
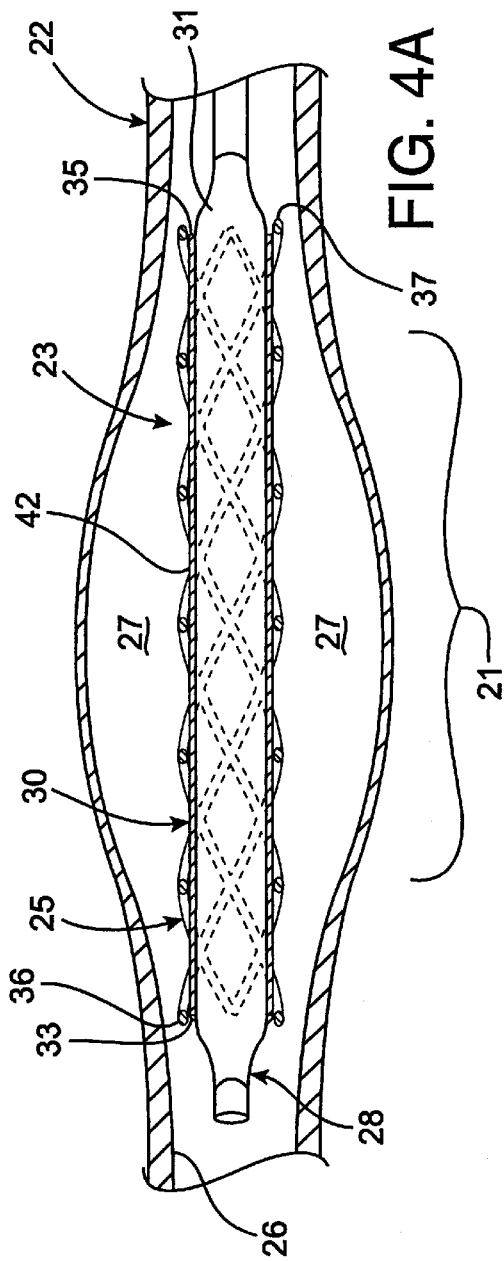

RADIOACTIVE INTRALUMINAL ENDOVASCULAR PROSTHESIS AND METHOD FOR THE TREATMENT OF ANEURYSMS

TECHNICAL FIELD

The present invention relates, generally, to the treatment of vascular disorders and, more particularly, to the treatment of aneurysms with radioactive intraluminal endovascular prosthesis.

BACKGROUND ART

While conventional bypass graft treatment of aneurysms has steadily improved, mortality rates continue to be relatively high in cases such as abdominal aortic aneurysms. These often asymptomatic aneurysms 15 of blood vessel 16, as shown in FIG. 1, generally progressively enlarge in most patients over time, increasing the risk of rupture. Traditional bypass grafts are then required which are extremely invasive and include all the risks of open surgeries such as paraplegia, renal insufficiency, and myocardial infarction. Moreover, even three (3) to five (5) years after these surgeries, complications may arise which include concomitant coronary atherosclerotic disease, graft infection, aortoenteric fistula, thromboembolish, and anastomotic aneurysms.

In the recent past, more innovative approaches have evolved for the treatment of aneurysms. For example, DACRON® grafts, endovascular stent grafts and covered stents (referred heretofore generally as "stent grafts"), which have rapidly developed in an effort to expand stent technology, may be employed as a means of aneurysm treatment. These hybrid devices combine graft material with a stent or stent-like device to provide an expandable, stent-like structure having an impervious luminal surface.

These combination of features, once implanted, are very conducive to achieve endovascular exclusion of aneurysms. Typically, a graft material is mounted to and positioned along an exterior circumferential surface and/or the interior circumferential surface of the prosthesis in a manner forming an endovascular, blood impervious lumen therethrough. A proximal end of the graft is preferably endovascularly positioned just upstream from the vascular disorder while a distal end thereof terminates at a position just downstream thereof. As the proximal end and the distal end of the stent graft become anastomosed with the vessel wall, the vascular disorder becomes endovascularly excluded from the blood flow while the stent graft impervious lumen maintains vessel patency.

Upon proper endovascular deployment and seal formation of the stent, cell matrix formation and tissue healing may commence in the aneurysmal sac and on the luminal surface. For example, in the aneurysmal sac between stent graft and the vascular wall, the residual blood clotting and inflammatory response cause cellular proliferation and connective formation, forming a matrix that may seal the sac. In addition to the sealing, the resulted wall, which is a combination of prosthesis, connective tissue matrix, and arterial wall provides a conduit support of proper hemodynamic blood flow.

Intraluminally, thromboembolic processes will occur on the luminal surface of the graft/stent. Briefly, during this thrombotic phase, platelets and blood clots adhere to the surface to form a fibrin rich thrombus. Endothelial cells then appear, followed by intense cellular infiltration. Finally, during the proliferative phase, actin-positive cells colonize the residual thrombus, resorbing the thrombus.

The primary problem associated with this technique is the time period required for endovascular sealing and repair of the aneurysmal sac. Tissue response to injuries of this nature are generally on the order of a few months to years. This is especially true for the luminal surface of the graft material where organized thrombus formation may be difficult to achieve. Such endothelial cell growth to line the lumen of the stent graft may require years of healing or may never be fully completed.

Accordingly, several clinical complications may result due to improper delayed cellular healing. One of the most prevalent problems, aortoentenic fistula, arises when the seal integrity between the vessel wall and the proximal end of the stent graft is compromised due to slow thrombus formation and incomplete tissue growth. Such upstream, proximal seal breaches cause blood infiltration through the incomplete anastomosis that may lead to abdominal blood loss. Stent grafts efficiency and effectiveness are substantially reduced since the luminal surface is not re-endothelialized, exposing the foreign surface to the risk of thrombosis and its complications.

There is a need, therefore, to increase the effectiveness and efficiency of the stent graft to reduce the time period for vascular repair.

DISCLOSURE OF INVENTION

Accordingly, a method is provided for promoting and increasing the rate of at least one of thrombus formation and proliferative cell growth of a selected region of cellular tissue. The method includes the step of endovascularly irradiating of the selected region endovascular radiation, having a dose range of about 1 Gy to about 600 Gy at a low dose rate of about 1 cGy/hr to about 320 cGy/hr, to promote thrombus proliferation followed by cellular proliferation of the affected selected region. Preferably, the dose of endovascular radiation is about 1 Gy to about 25 Gy at the graft surface, and at a low dose rate of about 1 cGy/hr to about 15 cGy/h. The selected region is preferably the luminal blood contents such as platelets, clotting proteins, and fibrin, while the target cells may include circulatory stem cells and cells from the adjacent connective tissue.

In one embodiment, the present method includes the step of positioning a deformable endovascular device, adapted to endovascularly emit the radioactive field, proximate the aneurysm. This step is performed by implanting the deformable endovascular device adjacent the aneurysm of the blood vessel. To generate the radioactive field and before the positioning step, the present invention includes the step of embedding radioactive material in the deformable endovascular device.

In another embodiment the embedding step further includes the step of: embedding a central portion of the endovascular prosthesis, sized to extend substantially adjacent the aneurysm when properly positioned, with a first radioactive activity generating the first named radiation acting upon the aneurysm; and embedding the end portions of the endovascular prosthesis, positioned on opposed sides of the central portion and extending beyond the upstream end and the downstream end of the aneurysm, with a second radioactive activity generating a second radiation having a dosage adapted to decrease thrombus formation and/or cell proliferation of the affected regions flanking the aneurysm.

In still another embodiment, the method of the present invention includes the step of positioning an intra-luminal endovascular prosthesis in the vessel proximate the aneurysm; and deploying the endovascular prosthesis from a contracted condition to an expanded condition, wherein the endovascular prosthesis engages the interior walls of the blood vessel forming a void between the endovascular prosthesis and the aneurysm for receipt of the radioactive seeds therein and such that the radioactive seeds are substantially retained is the void by the endovascular prosthesis. In another method, radiosensitizers may be deposited within the void or the aneurysmal sac, or be inserted into the aneurysmal contents. These radiosensitizers will be made radioactive or activated through external beam radiation or endovascular irradiation.

In another aspect of the present invention, a proliferation device is provided for increasing the rate of proliferative cell growth and/or induce thrombus formation of a selected region of cellular tissue. The proliferation device includes a deformable endovascular device adapted for secured positioning adjacent to the selected region of cellular tissue, and a radioactive source. This source cooperates with the deformable endovascular device in a manner endovascularly irradiating the selected region with endovascular radiation, having a dose range of about 1 Gy to about 600 Gy at a low dose rate of about 1 cGy/hr to about 320 cGy/hr, to increase thrombus formation and/or cell proliferation of the affected selected region.

The radioactive source is provided by radioactive material embedded in the deformable endovascular device. In one embodiment, the deformable endovascular device is provided by radioactive coils, endovascularly irradiating the radiation, sized and dimensioned for receipt in a pseudoaneurysm. In another embodiment, for saccular or fusiform aneurysms, the deformable endovascular device is provided by a tubular-shaped intraluminal endovascular prosthesis radially expandable from a contracted condition and an expanded condition. In the contracted condition, percutaneous delivery into the blood vessel is enabled, and an expanded condition, the deformable endovascular device radially contacts the interior walls of the blood vessel for implanting thereto. In another method, the described endovascular sources can be radiosensitizers or radioactive sources that are coated with biologic factors such as growth factors, adhesion molecules, and organic matrix.

The thrombus formation and/or cellular proliferation device further includes a tubular-shaped sheath device defining a lumen therethrough, and cooperating with the endovascular prosthesis to substantially prevent fluid communication between fluid flow through the lumen of the blood vessel and the aneurysm, while maintaining vessel patency. For the aneurysms, the prosthesis is sized and dimensioned to extend beyond an upstream end of the aneurysm and beyond a downstream end of the aneurysm each by at least about 1.0 mm when properly positioned in the vessel.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 3 is a fragmentary, side elevation view, in cross-section, of the stent graft device of FIG. 2 being percutaneously delivered in a contracted condition.

FIGS. 4A and 4B is a sequence of side elevation views, in cross-section, of the stent graft device of FIG. 3 being moved from the contracted condition to an expanded condition.

BEST MODE OF CARRYING OUT THE INVENTION

Figure 1:
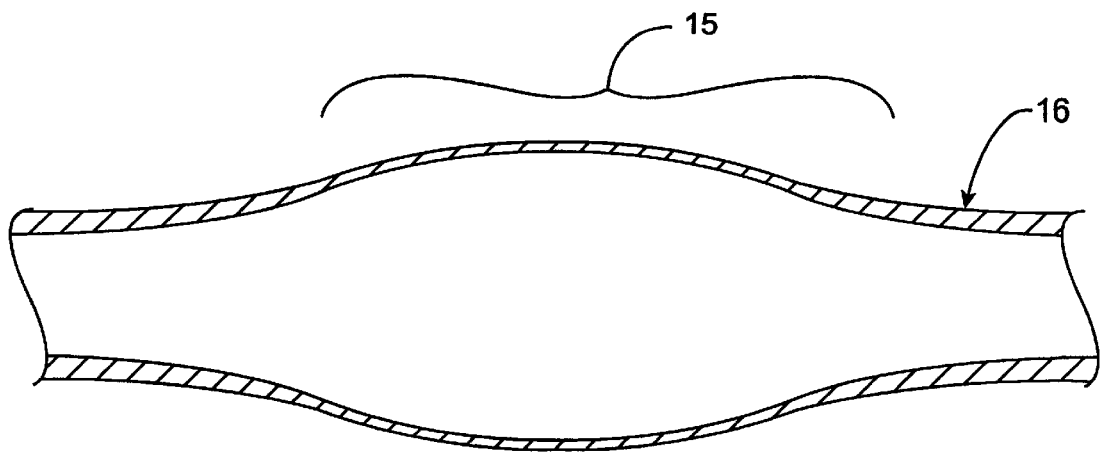
FIG. 1 is a fragmentary, side elevation view, in cross-section, of a typical fusiform aneurysm.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Attention is now directed to FIGS. 2–4B, 7 and 8 where a method and apparatus are illustrated for increasing the rate of proliferative cell growth and/or induce thrombus formation for a selected region 21 of cellular tissue 22. Briefly, the method includes the step of endovascularly irradiation the selected region with radiation, having a dose range of endovascular radiation of about 1 Gy to about 600 Gy at a low dose rate of about 1 cGy/hr to about 320 cGy/hr, for increasing the rate of cell proliferation and/or induce thrombus formation of the affected selected region. An endovascular device, generally designated 23, is adapted for endovascular positioning in close proximity to the selected region 21 of cellular tissue 22. The endovascular device includes a radioactive material or source collectively delivering a radioactive field upon the selected region 21 of a dosage adapted to increase the rate of cell proliferation and/or induce thrombus formation in the affected selected region 21.

While external exposure of living cells or cellular tissue, in a single or fractionated dose, to a low level radioactive field has been shown to accelerate proliferative cell growth, *Circulation Research*, January 1962; X:51–67; *Radiotherapy & Oncology* 1994; 32:29–36; *Int. J. Radiation*

*Oncology Biology Physics*, 1987; 13:715–722; *JACC* April 1992:19:5:1106–13, endovascular radiation exposure is advantageous in many respects. For example, this approach tends to be less invasive than open surgery. A longer duration of radiation exposure, moreover, may be achieved at lower radiation levels to provide similar radiation doses, as opposed to the single or fractionated doses of the external method generally at higher relative radiation levels. A continuous irradiation enables a continuous promotion of thrombosis on the vascular surface to establish a matrix for cellular adhesion, while a constant low dose irradiation provides a continuous stimulation of cellular proliferation. As will be discussed in greater detail below, selectively increasing cell proliferation and/or inducing thrombus formation has enormous medical device and biotechnological implications. Further, this approach is applicable to a wide range of cellular tissue, such as endothelial cells, myofibroblast cells, fibroblast cells, other fibroblast-type cells, inflammatory cells, smooth muscle cells of different phenotypes, spindle-type cells and other connective tissue.

In accordance with the present invention and as will be shown in Experiment A described below, by providing a dose of radioactivity in the range of about 1 Gy to about 600 Gy at about 0.1 mm from the stent surface, and at a low dose rate of about 1 cGy/hr to about 320 cGy/hr, the rate of proliferative cell growth and/or thrombus formation may be selectively increased. For example, the rate of proliferative cell growth secondary to thrombosis (fibrin deposition, platelets adhesion, and erythrocytes and inflammatory cell aggregation) has been observed to increase by between about 100% and about 500% in a time frame of about 3 months as compared to a control non-radioactive implant. More preferably, the radioactive dose is in the range of about 1 Gy to about 25 Gy at about 0.1 mm from the stent surface, and at a low dose rate of about 1 cGy/hr to about 15 cGy/hr.

Figure 11:
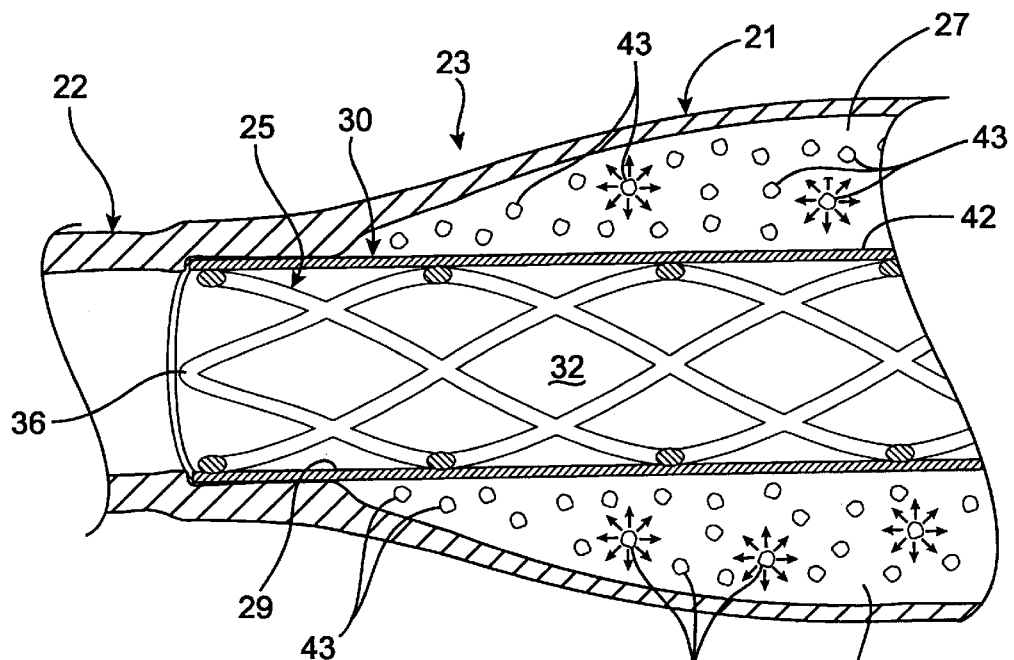
FIG. 11 is a fragmentary, side elevation view, in cross-section, of an alternative embodiment stent graft device of FIG. 4B incorporating the deposition of radioactive seeds.
Figure 12A:
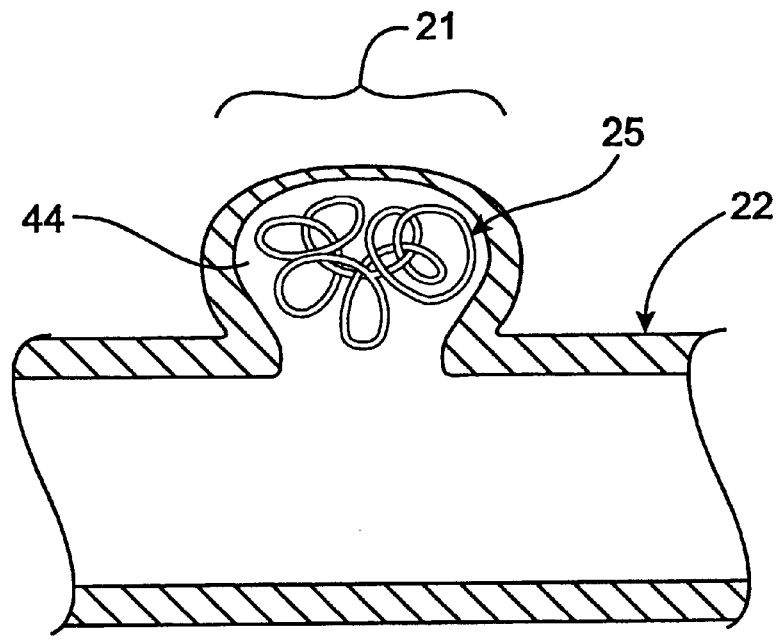
FIGS. 12A and 12B is a sequence of side elevation views, in cross-section, of a pseudoaneurysm having a radioactive coil device of the present invention deployed therein.
Figure 12B:
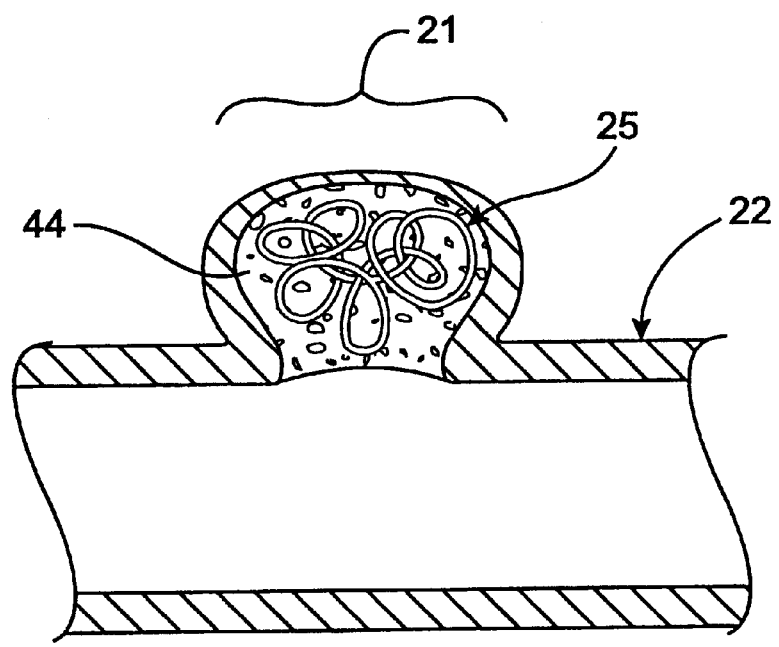

To generate a uniform radioactive field, a radioactive material or source is preferably positioned in close proximity to the selected or target region of cellular tissue such that the proper dose of radioactivity can be applied thereto. This radioactive source is preferably provided by implantable structures which can be alloyed, embedded, or implanted with the proper radioactivity of radioisotopes so that the proper dose of endovascular radiation may be endovascularly emitted to the designated selected region. Such implantable structures, for example, include intraluminal endovascular prosthesis such as stents, stent grafts, or covered stents can be made radioactive to provide low dose radiation on the luminal surface in promoting fibrin deposition, cellular adhesion, and cellular proliferation on the selected region 21. Other implantable structures include emboli coils 25 (as shown in FIGS. 12A and 12B, and to be discussed in greater detail below) or the like, which may be irradiated or made radioactive to direct the radiation to target region 44. Still other implantable structures include radioactive seeds 43 and radiosensitizers (as shown in FIG. 11, and also to be discussed in greater detail below) which may be deployed to target selected region 21 of the cellular tissue.

Accordingly, the emission of the proper dose of endovascular radiation, as will be apparent below, requires consideration of factors such as the coil or structure density of the implant device, the proximity to the desired selected region, the dose rate, volume of the target tissue, specific type of isotopes, and the half-life of the particular type of radioisotope employed.

Typically, the emission of the radioactive dose from the implantable structures will be omnidirectional in nature, and generally only affect the cellular tissues in close proximity to structure. Moreover, the radioisotopes employed for the purpose of the present invention are preferably alpha, beta or low energy gamma emitters. Other considerations include the predetermined depth of penetration of the radiation to the target region, the vascular and device geometry, as well as the specific type of isotope, and the half-life of the radioisotope.

Regarding the specific type of isotope, briefly, different types of isotopes generate different types of radiation. Phosphorus 32 ($^{32}$P), for instance, is a pure beta-particle emitter while Paladium 103 ($^{103}$Pd) is an X-ray photon emitter. Each type of radiation, moreover, generates different amount of energy which in turn affect the depth of penetration, as well as the amount of radiation absorbed by the targeted tissue. Gamma or X-ray photon as a wave, as an example, typically penetrate further into the tissue, as compared to alpha particles with a mass which penetrate into the tissue the least. Beta particles, on the other hand, typically penetrate into the tissue between the gamma particles and the alpha particle. Preferably, the device will be used with a beta or low energy gamma emitter.

Concomitantly, the described properties of the isotopes must be employed to determined the desired amount of radiation which is to be irradiated from the device. For instance, in order to achieve an equivalent dose of about 1470 cGy at about 0.1 mm from the stent surface of a 15 mm length stent, a $^{32}$P irradiating stent requires a radioactivity of about 0.93 µCi whereas a $^{103}$Pd irradiating stent requires a radioactivity of about 160 µCi.

As set forth above, another consideration is the desired half-life of the radioisotope particle which preferably ranges from about one (1) hour to less than about one (1) year. The half-life of the preferred optimum emitter may be about one (1) day to less than about twelve (12) weeks, and most preferably about two (2) weeks to less than about nine (9) weeks. Depending upon the size of the vascular disorder, the depth of the vessel wall, the dose rate, the required energy level and predetermined half-life may be selected to optimize vascular repair. Radioisotopes such as Phosphorus 32 ($^{32}$P), Yttrium 90 ($^{90}$Y), Calcium 45 ($^{45}$Ca), Palladium 103 ($^{103}$Pd) and Iodine 125 ($^{125}$I), for example, have been found to be particularly beneficial. For instance, Phosphorus 32 is a pure β-particle emitter, and it typically has a maximum energy of 1.69 MeV, an average energy of 0.695 MeV, a half-life of 14.3 days and a maximum particle penetration of a about three (3) millimeters into cellular tissue.

Figure 2:
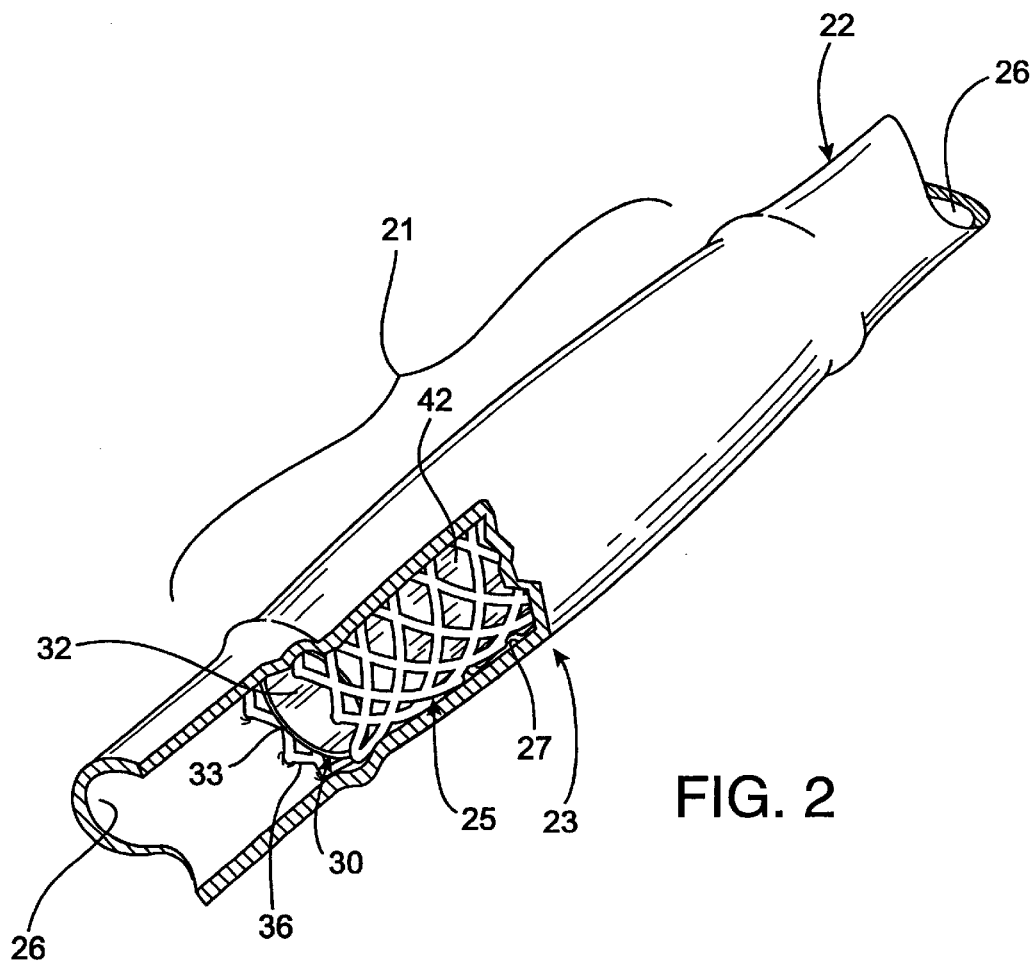
FIG. 2 is a fragmentary top perspective view, partially broken away, of an aneurysm incorporating a radioactive stent graft device constructed in accordance with the present invention.

One preferred application for the present invention is for use in the field of endovascular aneurysm repair, and more specifically, for use in combination with stent graft or covered stent devices or the like. As shown in FIG. 2, a blood vessel 22 is illustrated having a fusiform aneurysm 21 which is endovascularly excluded from the vessel lumen 26 by a radioactive intraluminal endovascular prosthesis 23 (e.g., a stent graft). This stent graft 23 is constructed to deliver a dose of endovascular radiation upon the selected region 21 (i.e., the arterial wall of the aneurysmal sac 27 that is formed between the stent graft and the wall of the blood vessel), while maintaining vessel patency. When the stent graft is properly positioned and placed in the vessel 22, the aneurysmal sac 27 will be endovascularly excluded from fluid communication with the blood flow through the vessel lumen 26.

Figure 8:
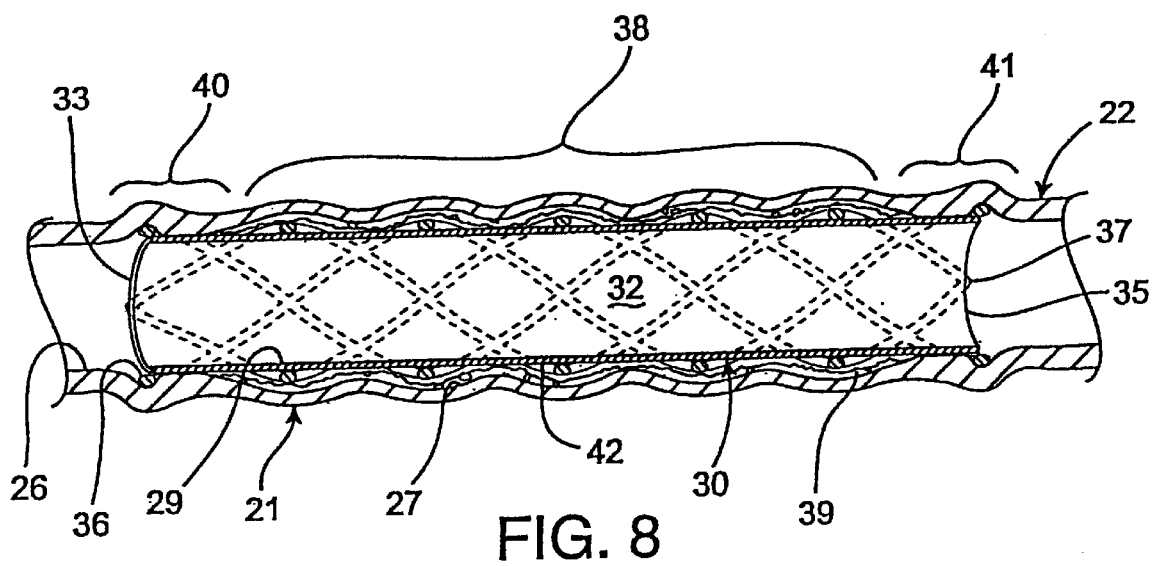
FIG. 8 is a fragmentary, side elevation view, in cross-section, of the stent graft device and repaired aneurysm of FIG. 4B in a stable proliferative phase.
Figure 10:
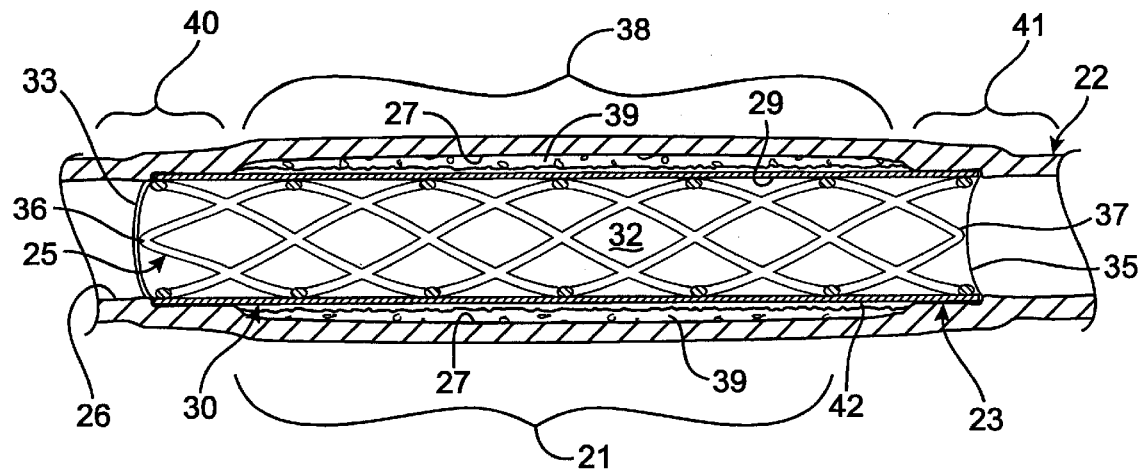
FIG. 10 is a fragmentary, side elevation view, in cross-section, of an alternative embodiment stent graft device of FIG. 4B having an external graft.

In accordance with the present invention, exposure of the excluded organic fluids (primarily blood) contained in the aneurysmal sac 27 to the above-indicated dose of endovascular radiation increases the rate of cellular migration and proliferation from the surrounding connective tissue and vascular wall. Ultimately, cell colonization will be induced to seal the aneurysmal sac 27 with fibroblasts or spindle-typed cell growth to repair the aneurysm (FIGS. 2, 8 and 10). In this configuration, thus, the selected region targeted for irradiation preferably includes the arterial wall and adventitial tissues such as smooth muscle cells and fibroblats and the blood contents contained in the excluded aneurysmal sac such as platelets, clotting proteins, and fibrin.

Figure 9:
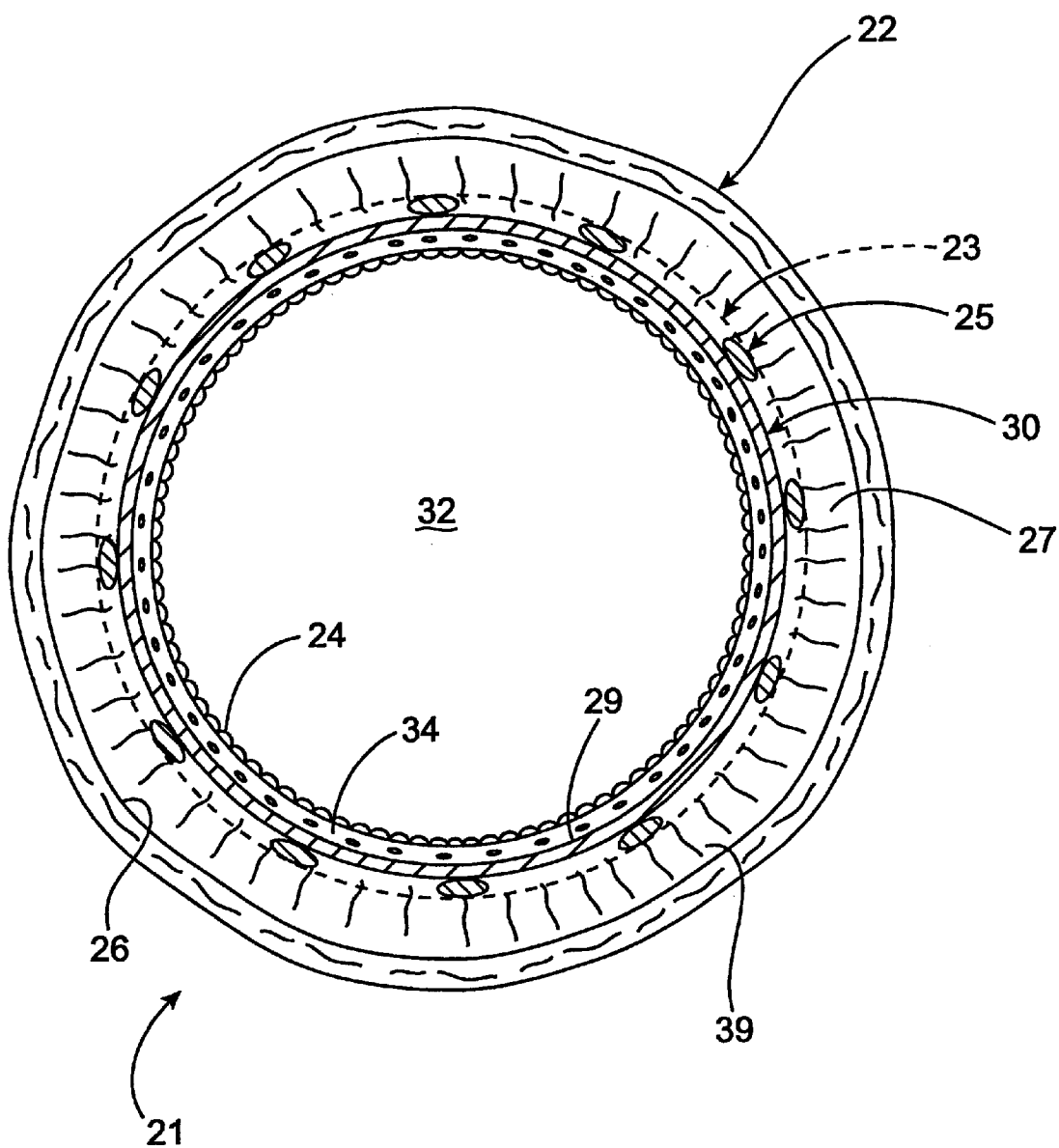
FIG. 9 is an enlarged, front elevation view, in cross-section, of the of the deployed stent graft device taken substantially along the plane of the line 9—9 in FIG. 8.

In the luminal aspect, as viewed in FIG. 9 and excluded in FIGS. 2, 8 and 10 for clarity, a similar mechanism is taking place in the impervious graft lumen 32. Thrombus formation in the graft lumen 32, as previously indicated, is difficult to achieve in a short time period since there is a lack of promotional factors such as natural thrombosis. Exposure of the interior surface of the graft lumen 32 to this low level radiation substantially induces thrombus formation (i.e., platelet adhesion and fibrin deposition) therealong which, in turn, commences cascade of endothelialization of the lumen. Briefly, during the Thrombotic Phase, the initial response is explosive activation, adhesion, aggregation and platelet deposition. In less than twenty-four hours, fibrin-rich thrombus accumulates around the platelet site. Next, during the Recruitment Phase, the initial appearance of cellular infiltration (monocytes and macrophages) occurs, followed by endothelial cells 24. Finally, during the Proliferative Phase, the actin-positive cells colonize the residual thrombus, resorbing the thrombus. Smooth Muscle Cell migration and proliferation into the degenerated thrombus creates substantially increased neointimal volume.

Exposure of the blood contents in the gap 27 to this dose of radiation has been determined to be beneficial in two respects. First, the rate of thrombotic formation in the luminal surface of the graft has been found to substantially increase which ultimately shortens the Thrombotic Phase. For example, a dose of endovascular radiation of between about 1 Gy and about 50 Gy has been shown to induce thrombus formation along the interior surface in 28 days or by a rate increased by 4–20 times (See Experiment A). By inducing thrombosis, which is the initial step towards endothelization of the lumen interior surface 29, proliferative cellular healing can commence. One hypothesis for the inducement of thrombus formation is due to the inflammatory response which induces the platelets, erythrocytes, and fibrin to adhere to the luminal surface 29 at a faster rate.

Second, the increased proliferative cell growth shortens both the Recruitment Phase and the Proliferative Phase in both the endothelialization of the lumen interior surface, as well as the repair of the aneurysmal sac 27. One theory for the increase in the rate of cell proliferation and is that the low level radiation causes a mild stimulation to the cells such as smooth muscle cells, inflammatory cells, and fibroblasts. In response, increased biochemical molecules such as cytokines to the region occurs which increases the rate of vascular repair and further enhances the cascade of healing.

Figure 4B:
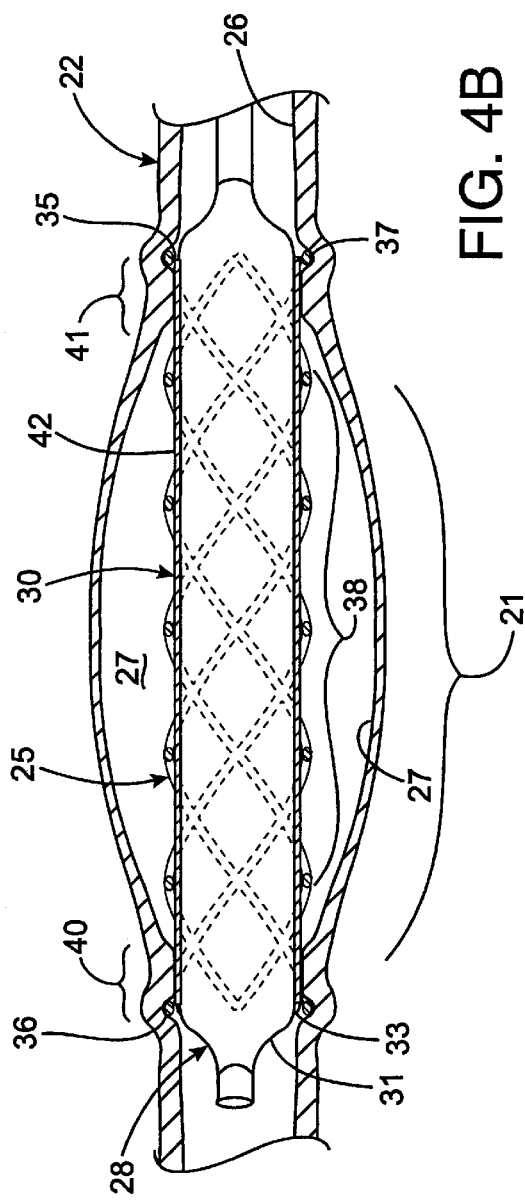

Referring back to FIGS. 3 and 4B, one technique of deployment of the stent graft 23 of the present invention is illustrated. The delivery may be performed through conventional open surgery or endovascular cut-down techniques. More preferably, the stent-graft delivery is performed percutaneously using a guide wire (not shown) positioned through vessel 22 and conventional stent-graft delivery system 28. A balloon expandable radioisotope stent graft 23 is provided having a deformable, tubular stent 25 and a thin walled material graft 30 coaxially aligned and mounted onto balloon 31 at a distal portion of stent-graft delivery system 28. FIGS. 3 and 4A illustrate the balloon and mounted stent graft 23 in a contracted condition which enables percutaneous advancement of the distal portion of the catheter through the vessel to the treatment site. Once endovascularly positioned, selective inflation of the balloon 31 radially expands the stent graft 23 from the contracted condition (FIG. 4A) to the expanded condition (FIG. 4B). Such exposure secures the stent against and into the intima of the vessel to prevent migration of the stent, and to promote anastomoses with the stent. Use of the radiation shields or the like may be employed to reduce unnecessary exposure to the radioactive field during percutaneous delivery. One such patented radiation shield for radioisotope stents is disclosed in U.S. Pat. No. 5,605,530 to Fischell et al.

It will be appreciated that the stent graft 23 is sized and dimensioned such that an upstream portion of the stent graft 23 is adapted for positioning just upstream of the aneurysm 21, while a downstream portion thereof is adapted positioning just downstream of the vascular disorder (e.g., aneurysm 21) each by at least about 1.0 mm. Preferably, these anchor regions of the stent, which may be provided by hooks, sutures or shape memory alloys such as NiTi, typically contact the intimal surface of the vessel along a sufficient longitudinal dimension to anchor the stent in place. When combined with the tubular sheath device or material graft 30, a blood impervious luminal surface 29 of the material graft endovascularly excludes the aneurysm 21 from the blood flow lumen to define the aneurysmal sac 27. Moreover, the material graft 30 and the expanded stent 25 cooperate to provide graft lumen 32 therethrough to maintain vessel patency.

Another stent delivery approach for vascular disorders is delivery through conventional cut-down techniques. Briefly, in this more invasive surgical technique, an incision may be made at the aneurysmal site for direct insertion of the stent graft therein. Upon proper deployment and anchoring of the stent graft, the incised arterial wall is opposed and is sutured together to close the incision, enveloping the graft within the lumen.

As set forth above, one problem associated with these prior art stent graft assemblies was the seal formation and seal integrity at the upstream portion of the stent graft with the interior wall of the blood vessel 22 (i.e., the intima). This seal is important to secure isolation of the aneurysmal sac 27 from the blood vessel lumen 26 which is desirable to be reproducible and to be performed as quickly as possible. In accordance with the present invention, in the aneurysmal sac aspect, the radioactivity endovascularly emitted from the stent surface directly upon the target endothelial cells of the intima at the proximal and distal end portions end 40, 41 of stent graft substantially increases anastomosed proliferative cell matrix growth thereof at these contact regions. Hence, seal formation between the vessel 22 and the contacting proximal and distal end portions of the stent graft is substantially facilitated by the increase rate of proliferative cell growth. While not illustrated at the end portions of the stent graft in FIGS. 2, 8 and 10 for clarity, upon proper accelerated healing in the advanced proliferative stage, the neointimal layer 34 (i.e., the matrix formation with its cellular constituents) and the new endothelial layer 24 (FIG. 9) lining the stent graft lumen 32 grow over the proximal edge 33 and the distal edge 35 of the material graft 30, and the corresponding proximal and distal edge 36, 37 of the stent 25 to seal the aneurysmal sac 27 from the vessel lumen 26 and the graft lumen 32

Further, once the aneurysmal sac 27 is endovascularly excluded, thrombosis naturally commences therein which may be further advanced by the emitted radiation. However, as the radioactivity is endovascularly emitted from the stent surface in the proper dose and at the proper dose rate to the target fluids contained in the excluded aneurysmal sac 27 (FIG. 7), the residual blood clotting and inflammatory response induce proliferative cell growth and connective formation. In the advanced stages of healing, as best viewed in FIGS. 8 and 9, an arterial media 39 forms the connective tissue growth which eventually binds the vessel wall 26 against the exterior circumferential surface of the stent graft.

In the luminal aspect, as shown in FIG. 9, the proper dose of endovascular radiation emitted from the stent 25 will induce thrombus formation on the interior surface 29 of the material graft 30 defining the lumen. As the platelets and fibrin are induced to adhere to the interior surface 29 by the emitted radiation, a fibrin rich thrombus layer with trapped erythrocytes is deposited along the entire length of the lumen. This initiation of the localized thrombotic process functions as the initial building blocks for endothelialization of the stent graft lumen. In the recruitment phase, endothelial cells subsequently appear, followed by intense cellular infiltration. Finally, during the proliferative phase, actin-positive cells colonize the residual thrombus, resorbing the thrombus and forming a thin intima layer of endothelial cells lining the interior surface. In accordance with the present invention, this low dose endovascular radioactive stent graft has been shown to increase the rate of endothelialization about several times faster than conventional techniques.

To further facilitate platelet adhesion and thrombus formation, and/or cell proliferation, the interior surface 29 of the material graft 30 may include a biomaterial coating of biological growth factor to form a template in which cells may adhere. One such organic substance is preferably provided FIBRONECTIN® or collagen or the like. Additionally, the use of the present invention device in combination with proteins (e.g., fibroblast growth factors), or gene thereapy (e.g., VEGF) can provide beneficial results.

Figure 5:
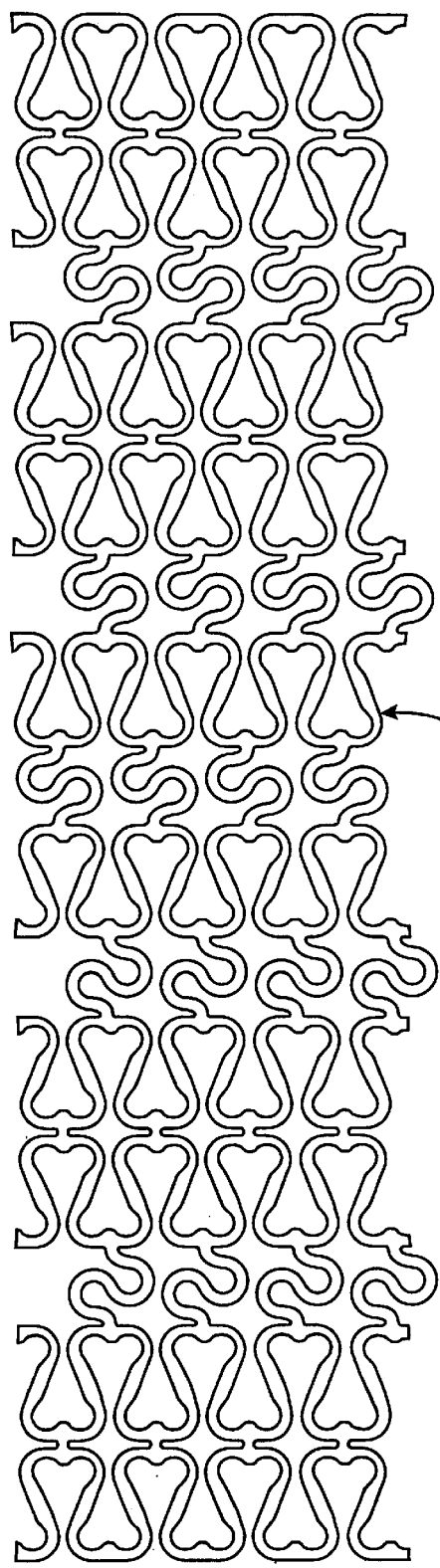
FIG. 5 is an enlarged 2-dimensional representation of a multi-cell, predeployed stent applicable for use with the present invention.

It will be appreciated that the endovascular prosthesis 23 may be provided by any conventional stent design capable of expansion and retention from a contracted condition to an expanded condition. For instance, a tubular slotted stainless steel Palmaz-Schatz stent from Johnson and Johnson Interventional Systems may be employed with the present invention. Another stent pattern, as shown in FIG. 5 which is the subject of a stent design disclosed in U.S. Pat. No. 5,697,971 to Fischell et al. and incorporated by reference herein in its entirety, may also be deployed with the present invention. As mentioned, one of the factors determining the amount of irradiation of the stent, necessary to endovascularly irradiate the appropriate dose of endovascular radiation to the selected region, is the stent design. For example, the denser the stent pattern or number of coils, the more uniform the dose of endovascular radiation. For the stent design of stent 25 illustrated in FIG. 5, the stent activity is preferably between about 0.07 $\mu$Ci/mm to about 0.8 $\mu$Ci/mm to provide a dose of endovascular radiation in the range of about 1 Gy to about 600 Gy from about 0.1 mm of the stent surface where the selected region 21 is preferably about 1.0 mm to about 3.0 mm from the surface of the stent. More preferably, the stent activity is between about 0.13 $\mu$Ci/mm to about 0.2 $\mu$Ci/mm.

Figure 6:
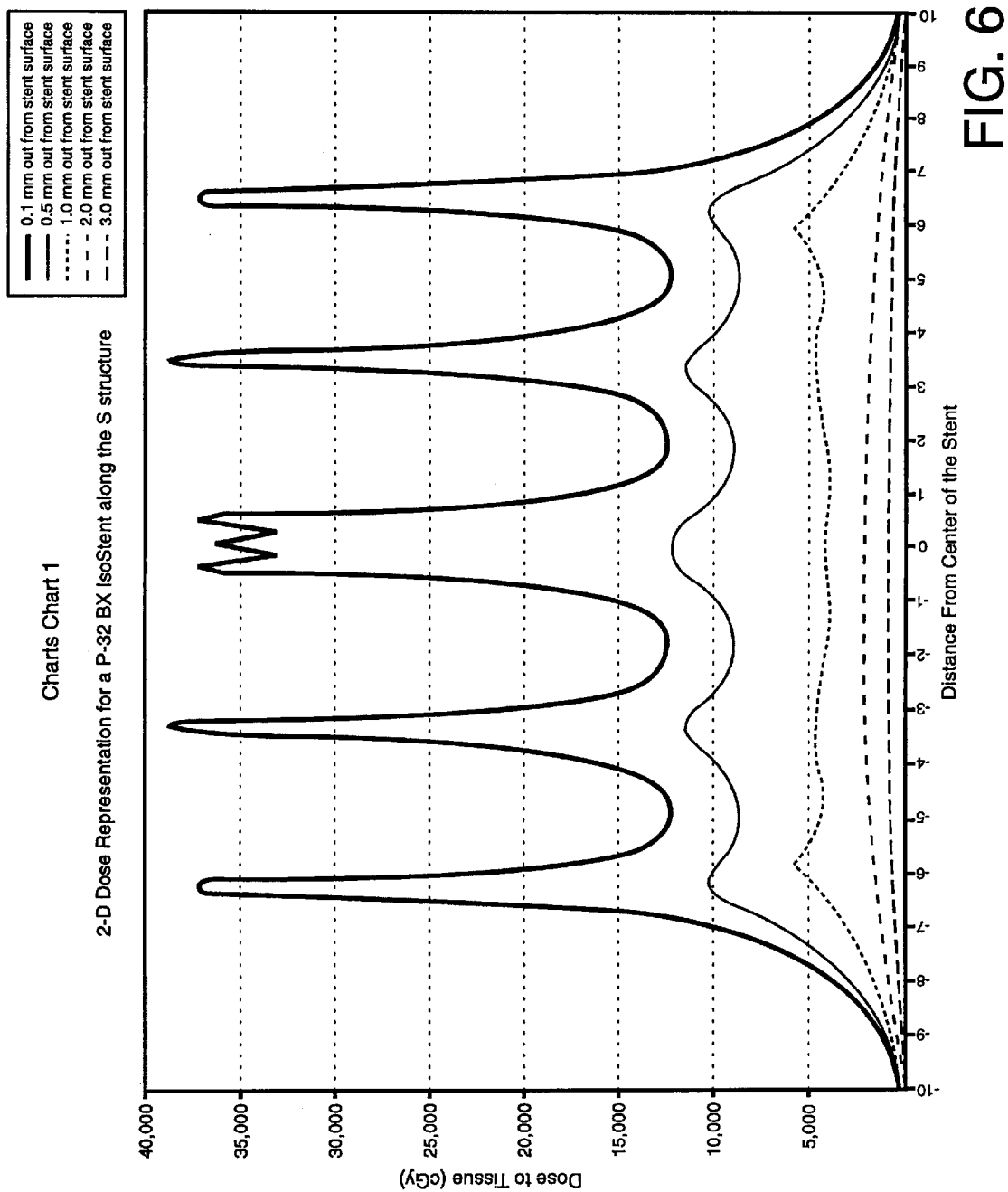
FIG. 6 is a 2-dimensional dose graphical representation for a Phosphorus 32 stent taken substantially along the plane of the line 6—6 in FIG. 5.

This dose distribution is better illustrated in FIG. 6 which represents a two-dimensional graph of the Dose to Tissue vs. Distance From the Surface of the Stent. In this configuration, the radioactive field becomes relatively more uniform as little as 0.5 mm from the stent surface which endovascularly irradiates a dose of about 10,000 cGy; and substantially more uniform from about 1–3 mm away from the stent surface. This graph represents measurements taken from stent design substantially similar to that of the '971 patent irradiated with phosphorus 32 ($^{32}$P) isotope with an activity of about 1.33 $\mu$Ci/mm with a 3 month total dose.

In the preferred embodiment, the material graft 30 is provided by a relatively flexible material composition which enables expansion from the contracted condition to the expanded condition and is impervious to blood flow. Such materials may include DACRON®, TEFLON®, PET (Polyethylene Terephthalate), polyester or a biocompatible metallic mesh material. This material graft 30 is affixed to the stent 25 using conventional anchor means employed in the field to prevent migration thereof along the stent. Further, as best viewed in FIGS. 3–4B, the proximal edge 33 and the distal edge 35 of the material graft 30 preferably terminate at or at a position slightly less than the corresponding proximal and distal edge 36, 37 of the stent 25. This configuration prevents any overhang of the ends of the material graft into either of the openings of the stent to minimize any current or potential occlusion of the stent passageway. This is especially problematic should excess in-growth be experienced at the ends of the stent graft were formation of the seal is to occur.

Figure 7:
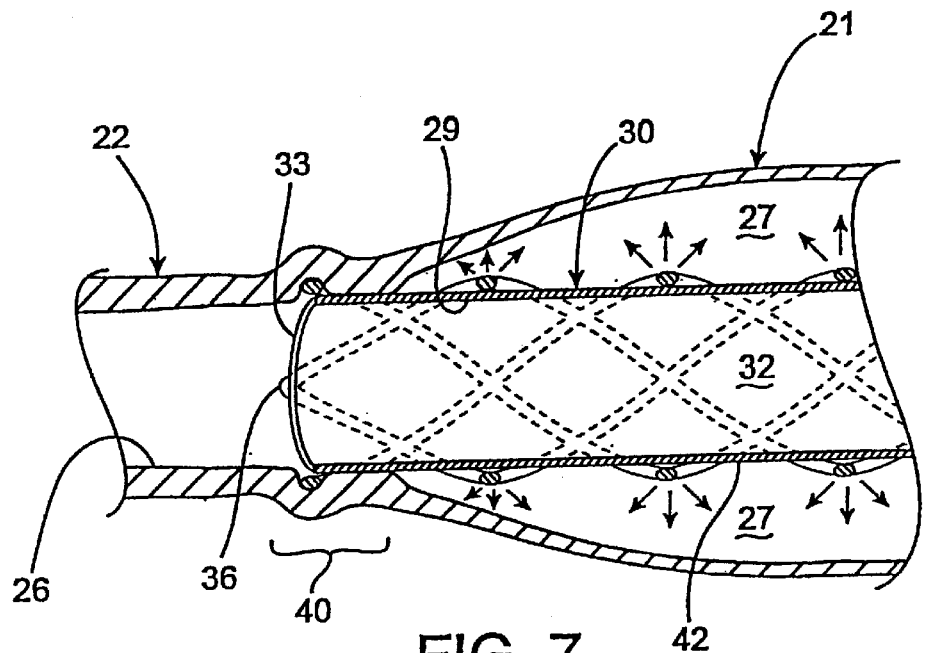
FIG. 7 is an enlarged, fragmentary, side elevation view, in cross-section, of the expanded stent graft device of FIG. 4B, and illustrating delivery of the endovascular radiation from the radioactive stent.

Once the stent graft 23 is properly positioned and moved to the expanded condition so that the aneurysmal sac is occluded from the lumen 26, the radioactive stent 25 of the present invention will begin endovascularly irradiating or delivering radioisotopes to the materials contained in the sac in the proper dose of endovascular radiation (FIG. 7). As mentioned above and in accordance with the present invention, the thrombotic phase is accelerated by the radioactivity, as is the recruitment phase and the proliferative phase for endothelialization of the aneurysmal sac 27 for aneurysm repair (FIG. 8).

In an alternative embodiment, the stent graft may be configured to irradiate different levels of radiation longitudinally and/or circumferentially along the stent. For example, in a peripheral aneurysm where the dilation is not circumscribed, full circumferential healing may not be necessary along the vessel wall. Hence, the endovascular irradiation from the stent may not need to be uniformly applied, as well. In another example, a stent graft having an uniform radioactivity longitudinally therealong will not emit a uniform dose rate of radiation near the proximal and distal ends there, as compared to the center of the stent graft, due to the distribution geometry. Accordingly, it may be desirable to selectively apply the desired amount of radioactivity along the geometry to either increase or inhibit cellular proliferation.

Moreover, to limit potentially occlusive in-growth at the proximal and distal ends of stent graft 23, the proximal and distal end portions of the stent which anchor the stent to the vessel may have different activities as compared to the growth inducing radioactivity of the central portion 38 of the stent (FIG. 8). The proximal and distal end portions 40, 41 of the stent graft 23 which physically contact the endothelial cells of the intima may be embedded or irradiated with an activity which reduces proliferative cell growth. However, it will be appreciated that the reduction of cell growth should not be at a magnitude where sealing time and reproducibility are detrimentally affected, or where seal integrity formation at the end portions is compromised.

Such secondary stent activities and resulting doses of endovascular radiation are disclosed in U.S. Pat. Nos. 5,176, 617 and 5,059,166 to Fischell et al., incorporated herein by reference. Preferably, the secondary activities are positioned on opposed sides of the central portion 38 and extending beyond the upstream end and the downstream end of the aneurysm.

Another approach to limit occlusive in-growth at the proximal and distal end portions of the stent graft would be to subsequently expose those portions to higher levels of radiation which decrease cell proliferation. For example, after the radioactive stent graft of the present invention has been deployed and the proximal and distal end portions have been sufficiently anastomosed to seal and endovascularly exclude the aneurysmal sac from the vessel and graft lumen, the end portions may be irradiated with radioactive isotopes at levels sufficient to decrease or prevent further cell proliferation. It will be appreciated, however, that such radiation dosages should not be so high as to damage the target tissue at the proximal and distal end portions.

Delivery of such radiation may be performed endovascularly through catheters or the like, or may be performed through more external techniques such as external beam irradiation.

This technique may also be applied to smaller branch vessels which are to be anastomotized to the side of stent graft (not shown). In these configuration, embodiment, after the vessel has sufficient anastomosed to the stent graft, the immediate area surrounding anastomosis site may be irradiated with the above mentioned higher level of radiation to decrease or prevent further cell proliferation.

In another alternative embodiment, the tubular material graft 30 may be positioned along the exterior surface of the stent 25, as shown in FIGS. 10 and 11. This covered stent also provides an impervious luminal surface 42 which prevents fluid communication between the stent-graft lumen 32 and the aneurysmal sac 27 so that thrombus formation and cell growth may be accelerated with the proper dose of radioactivity.

In yet another alternative embodiment, radioactive seeds 43 maybe implanted into the excluded aneurysmal sac 27 in combination with either a stent graft or covered stent. This radioactive seeding may be employed alone with a non-radioactive stent 25, or together with a radioactive stent. As shown in FIG. 11, the cumulative affect of the radioactive seeds produce the preferred dose of radioactivity to increase the cell/thrombus proliferation. In the preferred form, these particles 43 may be provided by stainless steel or platinum seeds about 0.1 mm to about 2 mm in diameter, and embedded with the proper activity of radioisotopes. Depending upon the desired density distribution of the implanted seeds in the aneurysmal sac 27, the activity of the seeds can be determined to produce the cumulative dose of endovascular radiation to be delivered to the selected region 21. In the preferred form, the density of the distribution of radioactive seeds is about 2 particles/cm$^3$, while the activity per seed is about 0.1 $\mu$Ci to about 0.5 $\mu$Ci.

Once the stent graft or covered stent 23 is properly deployed or partially deployed, the radioactive seeds 43 may be deposited into the occluded aneurysmal sac 27 to induce thrombus formation and accelerate proliferative cell growth. Preferably, the seeds are implanted through conventional injection techniques, through lumens of a (seed) delivery catheter or placement during open surgery.

In still yet another embodiment, the graft may be embedded with a radiosensitizer capable of being activated by either an external or endovascular radiation source. Once activated, the radioactive stent would subsequently emit the proper dose of radiation to increase the rate cell proliferation and/or induce thrombosis. Another approach would be to deliver or seed the aneurysmal sac 27 with a radiosensitizer, similar to the radioactive seeds, and then activate the same to emit the proper dose of radiation. One such radiosensitizer, for example, may include halogenated pyrimidines, while the activator may be provided by an X-ray, ultraviolet, and external electron beam source.

Turning now to FIGS. 12A and 12B, a saccular or pseudoaneurysm 21, such as an intracranial aneurysm, is illustrated which is formed along an upper portion of vessel 22. In accordance with this embodiment of the present invention, a radioactive coil emboli 25 may be implanted and anchored in the aneurysmal sac 44 of the pseudoaneurysm 21 to induce intravascular thrombosis (FIG. 12A). By irradiating or embedding these typically stainless steel or platinum coils with radioactivity, thrombus formation can be accelerated when the coils 25 deliver endovascular radiation of the proper radioactive dose to the aneurysmal sac 44 of the peusdoaneurysm 21. Once the thrombus phase is complete, the rate of the recruitment phase and the proliferative phase are also increased by the radioactivity emanating from the coil. As shown in FIG. 12B, the pseudoaneurysm 21 will then be repaired once the cell growth fill in the aneurysmal sac 44 of the pseudoaneurysm 21.

Similar to the radioactive seeds, the activity of the coils depends upon the predetermined coil density when positioned in the aneurysmal sac 44 of the pseudoaneurysm. Of course, a higher coil density to increase thrombogenicityic will require a smaller activity to generate a uniform radioactive field in the desirable range of about 1 cGy to about 600 cGy.

Still other embodiments may include a radioactive external beam device (not shown) which may be positioned on the outside of the vessel and disposed adjacent to the aneurysm sac or gap. This device may be used in combination with a radioactive or non-radioactive stent graft device to promote the rate of vascular repair of the vessel. In this configuration, the beam may be configured to focus the endovascular radiation toward the aneurysmal sac.

In still other combinations, the radioactive coil emboli may be employed in the aneurysmal sac in combination with a radioactive or non-radioactive stent graft (not shown). In this manner, the coil emboli will function in the same manner as the radioactive seeds.

A radioactive catheter wire (not shown) may be advanced percutaneously through the vessel and into the aneurysm to promote and accelerate thrombosis and vascular repair. This temporary radioactive wire may then be removed upon completion of the proper dose of endovascular radiation. This configuration may also be applied in combination with radioactive or non-radioactive stents, stent grafts, covered stents, coil emboli or the seed embodiments above-mentioned.

As mentioned above and in accordance with the present invention, the radioactive stent, coil emboli or seed embodiments may apply any other cellular growth inducing materials which are utilized to promote cellular growth. For example the exterior stent surface or the exterior material graft surface, as well as the graft interior surface, may be coated with a conventional tissue growth inducing biomaterial such as FIBRONECTIN®, VEGF or the like.

Other medical application upon which the present invention may apply include the rate of increase of cell growth proliferation of vascular dissections, wound healing, wound closures, atrial septal defects, atrial venus malformation, orthopedic implants to encourage osteoblast growth with the use of bone chip gel with radiation, and varicose veins, to encourage cell proliferation in obliteration of the lumen.

The following Experiment A serve to more fully under the above-described invention, as well as to set forth the best mode contemplated for carrying out various aspects of the invention. It is to be understood that this example in no way serves to limit the true scope of the invention, but rather are presented for illustrative purposes.

EXPERIMENT A

Overview:

A radioactive stent in accordance with the present invention was placed within the artery and the vascular response to the irradiation was examined at different time points after the stent placement. The endovascular irradiation (brachytherapy) was observed using the IsoStent BX™ radioactive stents. The isotopes were Phosphorus 32 ($^{32}P$) and Yttrium 90 ($^{90}Y$). Briefly, $^{32}P$ is a pure beta-emitting particles with a half-life of 14.3 days, an average energy of 0.60 MeV, and a maximum energy of 1.7 MeV. The $^{90}Y$ is also a pure beta-emitting particles with a half-life of 2.7 days, an average energy of 0.90 MeV, and a maximum energy of 2.3 MeV. These radioactive stents were implanted in the coronary arteries of forty Yucatan miniature pigs, and the vascular response was analyzed for three (3) months after the implantation.

Stent Preparation:

Proprietary stent of 15 mm length, tubular stainless steel IsoStent BX™ stents were made radioactive by either the direct ion implantation method or the radiochemical method. In the study with $^{32}P$, this radioisotope was directly ion implanted beneath the surface of the metal (Forschungszentrim Karlsruhe, Karlsruhe, Germany) to yield an activity level of 0.1, 1.0, 1.5, 3.0, 6.0, and 12.0 $\mu$Ci at stent implantation into the animals. Such activity levels yielded a total 3 month dose of $^{32}P$ in the range from 1.0 Gy to 600 Gy at 0.10 mm from the surface of the stents. The corresponding initial maximum dose-rate at 0.10 mm from the stent surface ranged from 1 cGy/hr to 120 cGy/hr. In the study with $^{90}Y$, the radioisotope was radiochemically coated onto the stent surface to yield an activity level of 1.0, 2.0, 4.0, 8.0, 16.0, and 32.0 $\mu$Ci. The total 3 month dose ranged from 3 Gy to 280 Gy at 0.10 mm from the stents surface, and the corresponding initial maximum dose-rate ranged from 5 cGy/hr to 320 cGy/hr. The control sample stents in this study were the non-radioactive BX™-stents of 15 mm in length and were fabricated in a manner similar to the radioactive stents except for ion implantation of $^{32}P$ or radiochemical process. All these stents were pre-mounted on PAS balloon catheters (Fischell IsoStent™ with delivery system, Johnson & Johnson Delivery System).

The stent radioactivity was determined as follows: In the $^{32}P$ stents, the activity level of each stent was determined by comparison to standard $^{32}P$ sources of known activity using liquid scintillation counting methods. After ion implantation, the stents were placed in a sealed cylindrical acrylic resin radiation shield and gamma-ray sterilized in a conventional manner. The stents were then implanted when the radiation level had decreased to the desired activity. The radiation levels at implantation were determined by calculations that used the known half-life for $^{32}P$ (14.3 days) and the following standard "activity" equation: $A_t = A_0 e^{-kt}$, where $A_t$ is the activity level at the time ($\mu$Ci), $A_0$ is the initial activity level ($\mu$Ci), t is time in days, and k is the rate constant.

Animal Model:

In the $^{32}P$ study, 40 Yucatan miniature swine underwent placement of 70 stents (50 radioactive $^{32}P$ ($\beta$-particle) BX stents, and 20 control, non-radioactive BX) in the left anterior descending, left circumflex or right coronary artery.

In the $^{90}Y$ study, there were 72 radioactive BX $^{90}Y$ stents and 28 control, non-radioactive stents that were implanted in the coronary arteries of 40 Yucatan miniature swine. Animals were medicated with aspirin 650 mg, nifedipine extended release 30 mg and ticlopidine 250 mg by mouth the evening prior to stent placement. Under general anesthesia, an 8F sheath was placed retrograde in the right carotid artery, and heparin (150 U/kg) was administered intra-arterial to achieve an activated clotting time greater than 300 seconds (Hemochron, International Technidyne, Edison, N.J.). After completion of baseline angiography, the 15 mm stents were implanted using the guiding catheter as a reference in order to obtain a 1:1.2–1.3 stent to artery ratio (i.e., 20%–30% oversizing) as compared with the baseline vessel diameter. Stents were manually crimped onto non-compliant 3.0 or 3.5 mm diameter 10 mm length angioplasty balloons (SCIMED, Maple Grove, Minn.). Placement of the stent was completed with two balloon inflation at 12 or 14 ATM for 30 seconds. Angiography was completed after stent implant to confirm patency of the stent and side-branches as well as to assess for migration or intra-luminal filling defects. The animals were allowed to recover and returned to care facilities where they received a normal diet and aspirin 81 mg daily. The animals were returned for coronary angiography and euthanasia 3 months after the stent implantation. Immediately following the angiography, the animals were euthanized with a lethal dose of barbiturate. The hearts were harvested and the coronary arteries were perfusion-fixed with 10% neutral buffered formalin at 60–80 mmHg for 30 minutes via the aortic stump.

Histology:

Non-contrast postmortem radiography was completed on each stented vessel prior to sectioning in order to assess stent expansion and structural integrity. The fixed hearts were X-rayed and the stented coronary artery segments were carefully dissected from the epicardial surface of the heart. Control sections of the adjoining non-stented artery were taken from the proximal and the distal ends. The stented arteries were then processed in graded series of alcohol and xylene and embedded in methyl methacrylate. The plastic embedded stents are then cut with a rotatory diamond edged blade into 6.0–8.0 mm blocks from the proximal, mid, and distal segments of the stent and then sectioned with a stainless steel carbide knife into 4–5 $\mu$m sections. Arterial sections proximal and distal to the stent were processed in paraffin and sectioned as above. All histologic section were stained with hematoxylin-eosin and Movat pentachrome stains. All three sections were examined by light microscopy and used for morphometric measurements. The paraffin embedded sections were similarly cut and stained in a routine manner and examined for any abnormalities.

Statistical Analysis:

The mean injury score, neointimal area and percent area stenosis were determined. Data are expressed as the mean±the Standard Deviation (SD). Lesion morphology and injury score were compared for the control and radioactive stents using ANOVA with a post hoc analysis for multiple comparisons. The stent activity, neointimal, and medial cell density were analyzed with a polynomial regression model to derive a slope, intercept and correlation coefficient to determine relations. Significance was established with a p value SD. Lesion morphology and injury score were compared for the control and radioactive stents using ANOVA with a post hoc analysis for multiple comparisons. The stent activity, neointimal, and medial cell density were analyzed with a polynomial regression model to derive a slope, intercept and correlation coefficient to determine relations.

Significance was established with a p value<0.05. All statistics were calculated using Starview 4.5 (Abacus, Berkeley, Calif.).

Results

Procedural and Postoperative:

One animal died due to balloon rupture during implantation of a control stent resulting in severe coronary spasm and refractory ventricular arrhythmias. Ventricular tachycardia and fibrillation occurred in one additional animal which required DC cardioversion to restore a normal sinus rhythm. All animals had a normal postoperative recovery and resumed a normal pig chow diet (PLirina) the following morning after stent implant. There were no cases of wound infection, incomplete healing or dehiscence. Daily observation of the animals indicated normal behavior and dietary intake. All animals had a stable or mild increase in body weight during the study (baseline 29.2+5.1 kg versus 31.2+5.5 kg at following-up, p<0.001).

Blood samples were obtained for complete blood counts in all animals prior to and at 28 days after stent placement. The mean white blood cell count was similar at stent implant and on follow-up study (baseline $12.5+3.0 \times 10^3$ cells/$mm^3$ versus follow-up $12.6+4.8 \times 10^3$ cells/$mm^3$, p=0.97). The mean hemoglobin concentration was normal baseline (10.5+1.5 g/dl) and was not significantly different 28 days after stent placement (10.3+1.2 g/dl, p=0.72). The baseline (mean $429+137 \times 10^3$ cells/$mm^3$) and follow-up mean (mean $493+110 \times 10^3$ cells/$mm^3$) platelet count were in a normal range for all animals.

Follow-tip Angiography:

Angiography was completed at 3 months after stent placement. Two animals did not have angiographic study because of the procedural or post operative complications previously described. In the 33 animals with 28 day angiographic follow-up, sixty-six of 66 stents (100%) were patent with normal angiographic coronary flow. There were no cases of stent migration or side-branch occlusion. Quantitative analysis of the coronary angiograms was note completed for this study.

Necropsy:

The gross appearance of the mediastinum, pericardium and myocardium was normal in all animals. The pericardial fluid was clear and straw colored in all cases. There were no cases with bloody or purulent pericardial fluid. The epicardial surface of the heart and stented arterial segments when visible were normal in all cases.

Histology:

The radioactive groups for $P^{32}$ and $Y^{90}$ showed a luminal surface with a complete re-endothelialization. The neointima of the radioactive groups had a substantially higher neointimal area and thickness compared to the non-radioactive stents, consisting of smooth muscle proliferation and matrix formation. A few inflammatory cells were found on the luminal surface as well as the neointima. The adventitial showed occasional fibrosis.

In comparing the $^{32}P$ to $^{90}Y$ groups, the $^{90}Y$ groups revealed a more complete re-endothelialization and healing. This may due to the shorter half-life of $^{90}Y$, which is 2.7 days as compared to 14.3 days.

The following vascular response parameters were determined: percent luminal reduction, percent adventitial change, presence of thrombus, percent internal elastic lamina disruption, percent external elastic lamina disruption, percent medial disruption, and percent of inflammation.

The following morphometric measurements were taken: external elastic lamina area, internal elastic lamina area, stented lumen area, medial area, thrombus area, intimal thickness and area, percent stenosis, and injury score.

TABLE 1

Morphometric measurements of $^{32}P$ radioactive stent study

| μCi/15 mm stent | EEL area, $mm^2$ | IEL area, $mm^2$ | Lumen area, $mm^2$ | Medial area, $mm^2$ | neo-intimal area, $mm^2$ | neo-intimal thickness, mm2 | % stenosis |
|---|---|---|---|---|---|---|---|
| 0 | 8.34 ± 1.63 | 6.54 ± 1.12 | 3.48 ± 1.06 | 1.81 ± 1.06 | 3.06 ± 1.58 | 0.41 ± 0.26 | 45.1 ± 18.1 |
| 0.1 | 7.32 ± 0.98 | 5.73 ± 0.84 | 3.90 ± 0.84 | 1.59 ± 0.28 | 1.82 ± 1.10 | 0.22 ± 0.18 | 3.07 ± 16.2 |
| 0.5 | 7.21 ± 0.97 | 5.97 ± 0.89 | 4.06 ± 1.04 | 1.25 ± 0.55 | 1.91 ± 1.07 | 0.22 ± 0.15 | 31.5 ± 15.5 |
| 1 | 7.17 ± 1.39 | 6.08 ± 1.05 | 1.89 ± 0.42 | 1.09 ± 0.39 | 4.19 ± 0.80 | 0.68 ± 0.81 | 68.7 ± 4.9 |
| 1.5 | 5.90 ± 1.02 | 4.85 ± 0.73 | 1.92 ± 0.91 | 1.05 ± 0.32 | 3.93 ± 0.72 | 0.48 ± 0.18 | 60.9 ± 15.3 |
| 3 | 7.73 ± 0.75 | 6.46 ± 0.62 | 1.82 ± 1.07 | 1.26 ± 0.18 | 4.64 ± 1.25 | 0.66 ± 0.13 | 71.4 ± 17.1 |
| 6 | 7.25 ± 2.16 | 6.17 ± 1.65 | 0.57 ± 0.53 | 1.09 ± 0.51 | 5.60 ± 2.12 | 0.81 ± 0.04 | 89.3 ± 9.80 |
| 12 | 8.38 ± 1.77 | 6.37 ± 1.24 | 2.14 ± 1.46 | 2.01 ± 1.01 | 4.22 ± 1.56 | 0.64 ± 0.34 | 66.6 ± 21.2 |

TABLE 2

Morphometric measurements of $^{90}Y$ radioactive stent study.

| μCi/15 mm stent | EEL area, $mm^2$ | IEL area, $mm^2$ | Lumen area, $mm^2$ | Medial area, $mm^2$ | neo-intimal area, $mm^2$ | neo-intimal thickness, mm2 | % stenosis |
|---|---|---|---|---|---|---|---|
| 0 | 8.55 ± 0.92 | 6.80 ± 0.77 | 4.07 ± 1.22 | 1.75 ± 0.33 | 2.34 ± 0.98 | 0.28 ± 0.20 | 40.0 ± 17.2 |
| 2 | 8.32 ± 1.02 | 6.71 ± 0.88 | 1.92 ± 0.91 | 1.61 ± 0.41 | 2.23 ± 1.25 | 0.27 ± 0.22 | 33.5 ± 18.1 |
| 4 | 8.43 ± 1.44 | 7.01 ± 1.17 | 1.82 ± 1.07 | 1.43 ± 0.33 | 2.15 ± 0.66 | 0.24 ± 0.10 | 31.1 ± 10.9 |
| 8 | 7.71 ± 1.21 | 6.24 ± 1.13 | 2.60 ± 1.01 | 1.47 ± 0.26 | 3.64 ± 1.26 | 0.54 ± 0.23 | 57.7 ± 15.5 |
| 16 | 8.22 ± 1.26 | 6.61 ± 1.29 | 2.50 ± 1.18 | 1.60 ± 0.83 | 4.11 ± 1.38 | 0.61 ± 0.20 | 61.6 ± 18.6 |
| 32 | 7.13 ± 1.27 | 5.97 ± 1.13 | 2.14 ± 1.46 | 1.16 ± 0.26 | 4.07 ± 1.68 | 0.57 ± 0.28 | 67.6 ± 22.7 |

For both $^{32}$P and $^{90}$Y studies, the radioactive stents showed a re-endothelialized lumen. The neo-intima showed a dose dependence increase of cellular proliferation and cell matrix formation. These findings were evidenced by the increase of neointimal area and thickness as a function of increased irradiation as compared to the controls. The medial layer beneath the struts was thinned. The adventitial showed a dose dependence increased in fibrosis.

Discussion

The effects of radiation on vascular cellular proliferation have been extensively studied. Lindsay et al applied X-ray radiation on the exposed dog aorta (Circulation Research, volume X, January 1962, page: 51–60). The animals were; sacrificed at different time points, ranging from 2 to 48 weeks following irradiation. The results showed that there was an accentuation of fibrocellular proliferation at a single dose of 8 Gy to 15 Gy and 30 Gy to 55 Gy. The latter group showed less vascular proliferation than the former. The range of the estimated dose-rate was from 176 cGy at the dorsal wall to 320 cGy at the surface of the ventral wall. The fibrocellular proliferation increased with time after the irradiation. The histopathologic findings showed intimal thickening with fibroblastic-like proliferation and some matrix formation. There was fibrosis of medial and adventitia in response to irradiation. Similar fibroblastic proliferation was observed when the aorta of the dogs were exposed to a single dose of external electron irradiation of 10–95 Gy (Circulation Research, volume X, January 1962, page: 61–67).

Other studies examined the vascular response when the radiation dose was fractionated. The results showed similar increased in cellular proliferation. In one study, the rat aorta was exposed to X-ray irradiation of 47 Gy with fractionation of 5.2 Gy (Radiotherapy & Oncology 32, 1994, page 29–36). There was an increased in fibrogenic cytokines and inflammatory cells that led to cellular proliferation, resulting in increased fibrosis. In another study with the aorta of the dogs, using 22–86 Gy in fractionation, there was a marked increased in intimal and medial proliferation (Int. J. Radiation Oncology Biology Physics, volume 13, page 715–722). The adventitial and perivascular tissue showed increased fibroblastic response. The 22–38 Gy group showed 4 fold and the 60–80 Gy showed about 20 fold increased in intimal thickness as compared to the control group.

Similar vascular response to external beam irradiation was also observed in the coronary arteries. Schwartz et al exposed the coronary arteries of the pigs to a single dose of x-ray radiation of 4 Gy to 8 Gy in one day (JACC Volume 19, No. 5, April 1992:1106–13). The results showed a 20% to 50% increase of neointimal proliferation as compared to the control group.

The current experiments, applying endovascular radiation to pig coronary arteries, showed similar results. These studies involved the use of beta-emitting radioactive stents for endovascular delivery of radiation. As shown in Table 1 and Table 2, a significant neointimal proliferative response was observed in the $^{32}$P and $^{90}$Y groups as compared to the non-radioactive group. More importantly, all the radioactive and the non-radioactive groups showed no bio-compatibility related problems.

There was no evidence of foreign body giant cell reaction or excessive inflammatory response. The histologic sections showed no evidence of radiation injury such as necrosis of the arterial wall or the matrix, and the adventitia and the arterial wall revealed no evidence of significant inflammatory reaction.

The presence of trapped erythrocytes and fibrin material within the neointima indicates that radiation induces thrombosis on the luminal surface. The histopathologic results showed an increase of 100% to 500% of cellular proliferation, which indicates that the radiation promotes cellular growth. Although the 0.1 and 0.5 $\mu$Ci of the $^{32}$P groups showed a lesser neointimal thickness and a lower precent restenosis as compared to the control group, the results suggested a faster and a more complete re-endothelialization of the luminal surface. It is believed that the lower amount of irradiation on the surface may stimulate and activate the proliferation of the endothelial cells.

The results indicate that the dose for inducing localized thrombosis and cellular proliferation is 1 Gy to 600 Gy for $^{32}$P and 3 Gy to 280 Gy for $^{90}$Y. However, it is believed that the total dose that will result in cellular proliferation range from 1 Gy to 600 Gy, regardless of the isotopes used. This is the case because the principle of radiobiology has shown a given cellular tissue will yield the same or similar results if given the same dose of radiation regardless of the isotope (i.e beta-emitting or gamma-emitting isotopes) or the method of delivery (i.e endovascular or external. beam radiation, single dose or fractionation). The corresponding dose rate for inducing cellular proliferation also follows the same principle; that is, the initial dose rate of 1 cGy/hr to 320 cGy/hr will promote cellular proliferation regardless of the isotopes used or the methods of irradiation. As for the amount of activity on the stent, the total activity to achieve the desired cellular proliferation (in $\mu$Ci) will vary, depending on the isotope used and volume of target tissue. For example, to achieve a total dose of 1470 cGy on the surface of the stent, the $^{32}$P stent will require to have an activity of 0.93 $\mu$Ci, and the $^{103}$Pd stent will require an activity of 160 $\mu$Ci.

In conclusion, radiation can be used to induce cellular proliferation in the intima, media, and adventitia of the artery. Both the single dose of radiation and the fractionation of the total dose promote fibroblastic proliferation. The beta-emitting stents with the stated dose and dose rate showed a pronounced neointimal response and little adventitial cellular proliferation. In contrast, the external beam irradiation showed cellular proliferation from adventitia to intima. Thus, these radioactive modalities can be used to promote cellular proliferation the selected region of the artery.

What is claimed is:

1. A method for increasing the rate of at least one of thrombus formation and cell proliferation in a selected region of cellular tissue comprising the step of:

endovascularly irradiating the selected region with an endovascular device adapted to emit an endovascular radiation dose of about 1 Gy to about 600 Gy from an endovascular device surface thereof, and at a low dose rate of about 1 cGy/hr to about 320 cGy/hr, for a period of time sufficient to cause the increase in the rate of at least one of thrombus formation and cell proliferation of the affected selected region.

2. The method according to claim 1 wherein, the dose of endovascular radiation is about 1 Gy to about 25 Gy at the endovascular device surface, and at a low dose rate of about 1 cGy/hr to about 15 cGy/hr.

3. The method according to claim 1 wherein, said selected region of cellular tissue includes an aneurysm.

4. The method according to claim 3, wherein, said cellular tissue is provided by a blood vessel and the blood content.

5. The method according to claim 1 further including the step of:

before the endovascularly irradiating step, positioning a deformable endovascular device, adapted to endovascularly emit said endovascular radiation, in close proximity to said selected region.

6. The method according to claim 5, wherein, said positioning step is accomplished by deploying the deformable endovascular device adjacent the selected region of the cellular tissue.

7. The method according to claim 6, further including the step of:

before the positioning step, embedding radioactive material in the deformable endovascular device.

8. The method according to claim 7, wherein, said radioactive material is provided by radioisotopes selected from the group consisting essentially of alpha, beta and gamma isotopes.

9. The method according to claim 7, wherein, said radioactive material is provided by radioisotopes selected from the group consisting essentially of Phosphorus 32 ($^{32}$P), Yttrium 90 ($^{90}$Y), Calcium 45 ($^{45}$Ca), Palladium 103 ($^{103}$Pd) and Iodine 125 ($^{125}$I).

10. The method according to claim 8, wherein, said radioisotope has a half-life of about one (1) hour to less than about one is (1) year.

11. The method according to claim 10, wherein, said radioisotope has a half-life of about one (1) day to less than about twelve (12) weeks.

12. The method according to claim 11, wherein, said radioisotope has a half-life of about two (2) weeks to less than about nine (9) weeks.

13. The method according to claim 5, wherein, said endovascular device further includes an adhesion molecule and a biological growth factor to further induce cell proliferation.

14. The method according to claim 13, wherein, said the adhesion molecules include an organic substance having FIBRONECTIN.

15. The method according to claim 13, wherein, said growth factor includes a gene therapy substance having VEGF.

16. The method according to claim 1 wherein, said selected region of cellular tissue includes an aneurysm formed in a blood vessel.

17. The method according to claim 16, further including the step of:

before the endovascularly irradiating step, implanting an intraluminal endovascular prosthesis, endovascularly emitting said endovascular radiation, in said vessel proximate said aneurysm.

18. The method according to claim 17, wherein, said prosthesis is sized and dimensioned to extend beyond an upstream end of said aneurysm and beyond a downstream end of said aneurysm each by at least about 1.0 mm when properly positioned in said vessel.

19. The method according to claim 18, further including the step of:

before the implanting step, embedding radioactive material in the intraluminal endovascular prosthesis.

20. The method according to claim 19, wherein, said embedding step further includes the step of:

embedding a central portion of the endovascular prosthesis, sized to extend substantially adjacent the aneurysm when properly positioned, with a first radioactive activity generating the first named radiation acting upon said aneurysm; and embedding the end portions of said endovascular prosthesis, positioned on opposed sides of said central portion and extending beyond the upstream end and the downstream end of said aneurysm, with a second radioactive activity generating a second radiation endovascularly irradiating a dosage adapted to decrease at least one of thrombus formation and cell proliferation of the affected regions flanking the aneurysm.

21. The method according to claim 19, wherein, said radioactive material is provided by radioisotopes selected from the group consisting essentially of alpha, beta and gamma isotopes.

22. The method according to claim 19, wherein, said implanting step includes the step of deploying said intraluminal endovascular prosthesis from a contracted condition to a expanded deployed condition.

23. The method according to claim 19, wherein, said implanting step includes the step of percutaneously inserting said prosthesis in said vessel.

24. The method according to claim 18, wherein, said implanting step includes the step of performing an arterial cutdown and inserting said prosthesis in said vessel.

25. The method according to claim 1 wherein, said endovascularly irradiating step is applied to said selected region for a predetermined amount of time.

26. The method according to claim 1 wherein, said selected region of cellular tissue includes an aneurysm formed in a blood vessel, and said method further including the step of:

before the endovascularly irradiating step, implanting radioactive seeds, generating said radiation, in close proximity to said aneurysm.

27. The method according to claim 26, further including the steps of:

positioning an intraluminal endovascular prosthesis in said vessel in close proximity to said aneurysm; and deploying or partially deploying said endovascular prosthesis from a contracted condition to an expanded condition, wherein said endovascular prosthesis engages the interior walls of said blood vessel in a manner forming a void between the endovascular prosthesis and the aneurysm for receipt of the radioactive seeds therein and such that the radioactive seeds are substantially retained in said void by the endovascular prosthesis.

28. The method according to claim 1 wherein, said selected region of cellular tissue includes an aneurysm formed in a blood vessel, and said method further including the step of:

before the endovascularly irradiating step, implanting radiosensitizer seeds in close proximity to said aneurysm; and activating said radiosensitizer seeds to emit said radiation with an activator.

29. The method according to claim 28, further including the steps of:

positioning an intraluminal endovascular prosthesis in said vessel in close proximity to said aneurysm; and deploying or partially deploying said endovascular prosthesis from a contracted condition to an expanded condition, wherein said endovascular prosthesis engages the interior walls of said blood vessel in a manner forming a void between the endovascular prosthesis and the aneurysm for receipt of the radiosensitizer seeds therein and such that the radiosensitizer seeds are substantially retained in said void by the endovascular prosthesis.

30. A device for increasing the rate of at least one of thrombus formation and cell proliferation in a selected region of cellular tissue comprising:

an endovascular device adapted for endovascular positioning in close proximity to the selected region of cellular tissue, and including a radioactive material adapted to emit an endovascular radiation dose of about 1 Gy to about 600 Gy from an endovascular device surface thereof and at a low dose rate of about 1 cGy/hr to about 320 cGy/hr to collectively endovascularly irradiate the selected region with endovascular radiation for a period of time sufficient to cause the increase in the rate of at least one of cell proliferation, cellular adhesion and thrombus formation of the affected selected region.

31. The device as defined in claim 30, wherein, said endovascular device is deformable and adapted to position the radioactive material in close proximity to the selected region.

32. The device as defined in claim 31, wherein, said deformable endovascular device includes securing structure to secure the position of the endovascular device adjacent to an aneurysm in a blood vessel.

33. The device as defined in claim 30, wherein, said endovascular device is provided by radio active coils, endovascularly emitting continuous endovascular radiation, formed for receipt in an aneurysmal sac of a saccular pseudoaneurysm.

34. The device as defined in claim 30, wherein, said endovascular device is provided by radioactive seeds, endovascularly emitting continuous endovascular radiation, formed for receipt in an aneurysmal sac of an aneurysm.

35. The device as defined in claim 30, wherein, said endovascular device is provided by radiosensitizer seeds formed for receipt in an aneurysmal sac of an aneurysm, and formed to endovascularly emit said endovascular radiation upon activation by an activator.

36. The device as defined in claim 31, wherein, said deformable endovascular device is provided by a tubular-shaped intraluminal endovascular prosthesis adapted to radially expand from a contracted condition, enabling delivery into said blood vessel, and an expanded condition, radially contacting the interior walls of said blood vessel for implanting thereto.

37. The device as defined in claim 36, wherein, said endovascular prosthesis is adapted to percutaneously deliver the endovascular radiation to the selected region in the contracted condition.

38. The device as defined in claim 36, wherein, said radioactive materials are embedded in said intraluminal endovascular prosthesis.

39. The device as defined in claim 36, wherein, said endovascular prosthesis further includes a biological growth factor to further induce cell proliferation.

40. The device as defined in claim 36, wherein, said endovascular prosthesis is configured for secured positioning adjacent to an aneurysm in a blood vessel in a manner such that said prosthesis engages the interior walls of said blood vessel to form a void between the endovascular prosthesis and the aneurysm, and said device further includes;

radioactive seeds, endovascularly emitting said endovascular radiation, formed for receipt in said void.

41. The device as defined in claim 30, wherein, the dose of endovascular radiation is about 1 Gy to about 25 Gy, and at a low dose rate of about 1 cGy/hr to about 15 cGy/h at about 0.1 mm from the device surface.

42. The device as defined in claim 41, wherein, said radioactive material is provided by radioisotopes selected from the group consisting essentially of alpha, beta and gamma isotopes.

43. The device as defined in claim 41, wherein, said radioactive material is provided by radioisotopes selected from the group consisting essentially of Phosphorus 32 ($^{32}$P), Yttrium 90 ($^{90}$Y), Calcium 45 ($^{45}$Ca), Palladium 103 ($^{103}$Pd) and Iodine 125 ($^{125}$I).

44. The device as defined in claim 36, further including:

a tubular-shaped sheath device defining a lumen therethrough, and cooperating with the endovascular prosthesis to substantially prevent fluid communication between fluid flow through the lumen of the blood vessel and the aneurysm, while maintaining vessel patency.

45. The device as defined in claim 44, wherein, said sheath device is configured to be positioned along an exterior surface of the endovascular prosthesis substantially from one end thereof to an opposite end thereof.

46. The device as defined in claim 44, wherein, said sheath device is configured to be positioned along an interior surface of the endovascular prosthesis substantially from one end thereof to an opposite end thereof.

47. The device as defined in claim 44, wherein, said radioactive material is adapted to endovascularly irradiate a dosage of radiation to the affected selected region in the range of about 1 Gy to about 600 Gy, and at a low dose rate of about 1 cGy/hr to about 320 cGy/hr at about 0.1 mm from the device surface.

48. The device as defined in claim 47, wherein, the dose of endovascular radiation is about 1 Gy to about 25 Gy, and at a low dose rate of about 1 cGy/hr to about 15 cGy/h at about 0.1 mm from the device surface.

49. The device as defined in claim 36, wherein, said prosthesis is sized and dimensioned to extend beyond an upstream end of said aneurysm and beyond a downstream end of said aneurysm each by at least about 1.0 mm when properly positioned in said vessel.

50. The device as defined in claim 44, wherein, the endovascular prosthesis includes a central portion configured to extend substantially adjacent the aneurysm when properly positioned, and having a first radioactive activity generating the first named radiation acting upon said aneurysm; and the endovascular prosthesis including end portions positioned on opposed sides of said central portion and extending beyond the upstream end and the downstream end of said aneurysm, and having a second radioactive activity generating a second radiation having a dosage adapted to decrease at least one of thrombus formation and cell proliferation of the affected regions flanking the aneurysm.

51. The method according to claim 1 wherein,
said period of time is about 3 months.

52. The device as defined in claim 36, wherein
said endovascular prosthesis includes a stent graft having a deformable stent, configured for secured positioning adjacent to an aneurysm in a blood vessel, and a tubular material graft cooperating with said stent such that said prosthesis engages the interior walls of said blood vessel to form a void between the endovascular prosthesis and an aneurysmal arterial wall of the aneurysm.

53. The device as defined in claim 52, further including:
radioactive seeds, endovascularly emitting said endovascular radiation, formed for receipt in said void.

54. The device as defined in claim 52, wherein
said material graft is adapted for positioning along an interior surface of the deformable stent.

55. A method for treating an aneurysm having an aneurysmal arterial wall comprising the step of:
positioning a radioactive intraluminal endovascular prosthesis in a blood vessel proximate to the aneurysm, said prosthesis being adapted to emit endovascular radiation in the range of about 1 Gy to about 600 Gy from a surface thereof and at a low dose rate in the range of about 1 cGy/hr to about 320 cGy/hr;

deploying or partially deploying said endovascular prosthesis from a contracted condition to an expanded condition, wherein said endovascular prosthesis engages the interior walls of said blood vessel in a manner forming a void between the endovascular prosthesis and the aneurysm; and irradiating said aneurysmal arterial wall and said void with radiation emitted by said prosthesis for a period of time sufficient to cause the increase in the rate of at least one of thrombus formation and cell proliferation thereof.

56. The method according to claim 55, wherein,
said period of time is about 3 months.

57. The method according to claim 56, wherein,
said endovascular prosthesis includes a stent graft having a deformable stent, configured for secured positioning adjacent to the blood vessel walls, and a tubular material graft cooperating with said stent to form said void between the endovascular prosthesis and the aneurysm.

58. The method according to claim 57, further including the step of:
depositing radiosensitizer seeds, endovascularly emitting said endovascular radiation, in said void.

\* \* \* \* \*